United States Patent
Altman et al.

(10) Patent No.: US 9,120,785 B2
(45) Date of Patent: Sep. 1, 2015

(54) PYRIDYL AMINOPYRIDINES AS SYK INHIBITORS

(75) Inventors: Michael D. Altman, Needham, MA (US); Maria Emilia Di Francesco, Houston, TX (US); Andrew M. Haidle, Cambridge, MA (US); Ryan D. Otte, Natick, MA (US); John Michael Ellis, Needham, MA (US); Kaleen Konrad Childers, Newton, MA (US); Alan B. Northrup, Reading, MA (US); Liping Wang, Dayton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/116,205

(22) PCT Filed: May 4, 2012

(86) PCT No.: PCT/US2012/036426
§ 371 (c)(1),
(2), (4) Date: Nov. 7, 2013

(87) PCT Pub. No.: WO2012/154520
PCT Pub. Date: Nov. 15, 2012

(65) Prior Publication Data
US 2014/0100250 A1    Apr. 10, 2014

Related U.S. Application Data

(60) Provisional application No. 61/484,431, filed on May 10, 2011.

(51) Int. Cl.
*C07D 417/14* (2006.01)
*A61P 37/00* (2006.01)
*A61K 31/444* (2006.01)

(52) U.S. Cl.
CPC .................................. *C07D 417/14* (2013.01)

(58) Field of Classification Search
CPC .................................................. C07D 417/14
USPC .......................................... 514/333; 546/256
See application file for complete search history.

(56) References Cited

U.S. PATENT DOCUMENTS

| | | |
|---|---|---|
| 5,710,129 A | 1/1998 | Lynch et al. |
| 5,958,957 A | 9/1999 | Andersen et al. |
| 6,011,037 A | 1/2000 | Bar et al. |
| 6,248,790 B1 | 6/2001 | Uckun et al. |
| 6,432,963 B1 | 8/2002 | Hisamichi et al. |
| 6,589,950 B1 | 7/2003 | Collingwood et al. |
| 6,770,643 B2 | 8/2004 | Cox et al. |
| 6,797,706 B1 | 9/2004 | Hisamichi et al. |
| 6,897,207 B2 | 5/2005 | Cox et al. |
| 6,897,208 B2 | 5/2005 | Edwards et al. |
| 6,911,443 B2 | 6/2005 | Yura et al. |
| 6,979,694 B2 | 12/2005 | Das et al. |
| 7,060,827 B2 | 6/2006 | Singh et al. |
| 7,122,542 B2 | 10/2006 | Singh et al. |
| 7,244,739 B2 | 7/2007 | Cheng et al. |
| 7,259,154 B2 | 8/2007 | Cox et al. |
| 7,276,502 B2 | 10/2007 | Brenchley et al. |
| 7,449,458 B2 | 11/2008 | Bhamidipati et al. |
| 7,485,724 B2 | 2/2009 | Singh et al. |
| 7,488,727 B2 | 2/2009 | Cochran et al. |
| 7,538,108 B2 | 5/2009 | Singh et al. |
| 7,557,210 B2 | 7/2009 | Singh et al. |
| 7,605,172 B2 | 10/2009 | Commons |
| 7,803,801 B2 | 9/2010 | Kodama et al. |
| 8,551,984 B2 | 10/2013 | Altman et al. |
| 8,735,417 B2 | 5/2014 | Alman et al. |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0211657 A1 | 9/2006 | Singh et al. |
| 2006/0234483 A1 | 10/2006 | Araki et al. |
| 2006/0247262 A1 | 11/2006 | Baenteli et al. |
| 2007/0004626 A1 | 1/2007 | Masuda et al. |
| 2007/0015758 A1 | 1/2007 | Baruah et al. |
| 2007/0129362 A1 | 6/2007 | Bhamidipati et al. |
| 2007/0197782 A1 | 8/2007 | Clough et al. |
| 2008/0139535 A1 | 6/2008 | Anandan et al. |
| 2008/0182837 A1 | 7/2008 | Steurer et al. |
| 2012/0277192 A1 | 11/2012 | Altman et al. |
| 2013/0090309 A1 | 4/2013 | Romeo et al. |
| 2013/0225548 A1 | 8/2013 | Fujihara et al. |

FOREIGN PATENT DOCUMENTS

| | | |
|---|---|---|
| EP | 1392684 | 9/2006 |
| EP | 1854793 A1 | 11/2007 |
| JP | 2004203748 | 12/2002 |

(Continued)

OTHER PUBLICATIONS

Altman, U.S. Appl. No. 13/516,455, Notice of Allowance, Jan. 22, 2014.
Cywin, et al, "Discovery and SAR of Novel [1,6]Naphthyridines as potent Inhibitors of Spleen Tyrosine Kinase (SYK)", Bioorganic & Medicinal Chemistry Letters, 2003, pp. 1415-1418, vol. 13.
Gura, T., "Cancer Models: Systems for Identifying New Drugs are often faulty", Science Magazine, 1997, pp. 1041-1042, vol. 278, Issue 5340.
International Preliminary Report on Patentability, PCT/US2012/036426, Nov. 21, 2013, 8 pages.
International Search Report, PCT/US2012/036426, Jul. 31, 2012, 6 pages.

(Continued)

*Primary Examiner* — Janet L Andres
*Assistant Examiner* — Daniel Carcanague
(74) *Attorney, Agent, or Firm* — Eric A. Meade; Catherine D. Fitch

(57) ABSTRACT

The present invention provides novel pyrimidine amines of formula I which are potent inhibitors of spleen tyrosine kinase, and are useful in the treatment and prevention of diseases mediated by said enzyme, such as asthma, COPD, rheumatoid arthritis, and cancer.

13 Claims, 1 Drawing Sheet

(56) References Cited

FOREIGN PATENT DOCUMENTS

| WO | WO9712871 | 4/1997 |
|---|---|---|
| WO | WO02096905 | 12/2002 |
| WO | WO02102313 A2 | 12/2002 |
| WO | WO03057659 | 7/2003 |
| WO | WO03078404 | 9/2003 |
| WO | WO2004005283 | 1/2004 |
| WO | WO2004080463 | 9/2004 |
| WO | WO2004087698 A2 | 10/2004 |
| WO | WO2004087699 | 10/2004 |
| WO | WO2005013996 | 2/2005 |
| WO | WO2006093247 | 2/2005 |
| WO | WO2005026158 | 3/2005 |
| WO | WO2005028475 | 3/2005 |
| WO | WO2005033103 | 4/2005 |
| WO | WO2005056547 | 6/2005 |
| WO | WO2006004865 | 1/2006 |
| WO | WO2006028833 | 3/2006 |
| WO | WO2006050480 | 5/2006 |
| WO | WO2006068770 | 6/2006 |
| WO | WO2006078846 | 7/2006 |
| WO | WO2006129100 | 12/2006 |
| WO | WO2006133426 | 12/2006 |
| WO | WO2006135915 | 12/2006 |
| WO | WO2007009681 | 1/2007 |
| WO | WO2007009773 | 1/2007 |
| WO | WO2007028445 | 3/2007 |
| WO | WO2007042298 | 4/2007 |
| WO | WO2007042299 | 4/2007 |
| WO | WO2007070872 | 6/2007 |
| WO | WO2007085540 | 8/2007 |
| WO | WO2007107469 | 9/2007 |
| WO | WO2007117692 A2 | 10/2007 |
| WO | WO2007120980 | 10/2007 |
| WO | WO2009084695 | 12/2007 |
| WO | WO2008024634 A1 | 2/2008 |
| WO | WO2008073687 | 6/2008 |
| WO | WO2008137605 A1 | 11/2008 |
| WO | WO2009012421 A1 | 1/2009 |
| WO | WO2009031011 | 3/2009 |
| WO | WO2009032861 A1 | 3/2009 |
| WO | WO2009097287 | 8/2009 |
| WO | WO2009102468 | 8/2009 |
| WO | WO2009103032 | 8/2009 |
| WO | WO2009131687 | 10/2009 |
| WO | WO2009136995 | 11/2009 |
| WO | WO2009145856 A1 | 12/2009 |
| WO | WO2010027500 | 3/2010 |
| WO | WO2010068257 | 6/2010 |
| WO | WO2010068258 | 6/2010 |
| WO | WO2011086085 A1 | 7/2011 |
| WO | WO2012041476 | 4/2012 |
| WO | WO2012154518 A1 | 11/2012 |
| WO | WO2012154519 | 11/2012 |

OTHER PUBLICATIONS

Johnson, et al, "Relationships between drug activity in NCI preclinical in vitro and in vivo models and early clinical trials", British Journal of Cancer, 2001, pp. 1424-1431, vol. 64(10).

Pamuk et al, "Spleen tyrosine kinase inhibition in the treatment of autoimmune, allergic and autoinflammatory diseases", Arthritis Research & Therapy, 2010, pp. 1-11, vol. 12, Issue :222.

Pearce, H.L. et al, "Failure modes in anticancer drug discovery and development", Cancer Drug Design and Discovery, 2008, Edited by Stephen Neidle—pp. 424-435, Chapter 18.

Romeo, U.S. Appl. No. 13/704,484, Notice of Allowance, Mar. 25, 2014.

Simone, J., Introduction, Part XIV, Oncology, Cecil Textbook of Medicine, 1996, pp. 1004-1010, vol. 1—20th Ed.

Yamamoto, et al, "The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents", The Journal of Pharmacology and Experimental Therapeutics, 2003, pp. 1174-1181, vol. 306(3).

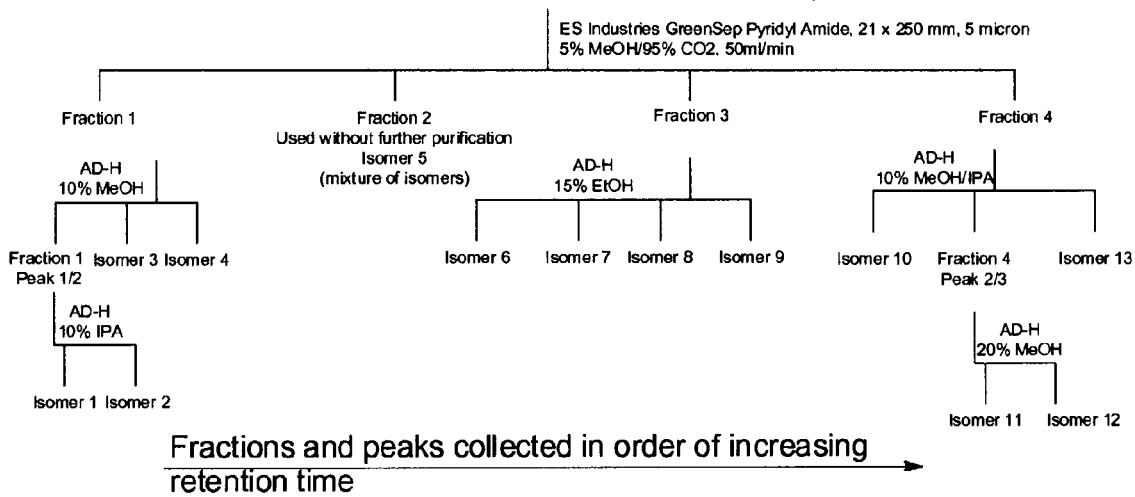

PYRIDYL AMINOPYRIDINES AS SYK INHIBITORS

CROSS REFERENCE TO RELATED APPLICATIONS

This application is a U.S. National Phase application under 35 U.S.C. §371 of PCT Application No. PCT/US2012/036426, filed May 4, 2012, which claims priority under 35 U.S.C. §119(e) from U.S. Provisional Application No. 61/484,431, filed May 10, 2011.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}R1$ and or $Fc_{epsilon}R1$ receptors, and is positioned early in the signaling cascade. In mast cells, for example, the early sequence of $Fc_{epsilon}R1$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in PGD2, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

U.S. Pat. No. 7,803,801 discloses Syk inhibitors having the formula:

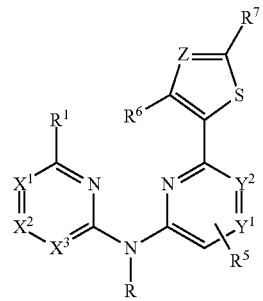

wherein the variables are as defined therein.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of Syk as well as pharmaceutical compositions containing them. As Syk inhibitors compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

BRIEF DESCRIPTION OF THE DRAWINGS

FIG. 1 shows the separation of the stereoisomers of ethyl 4-[1-hydroxy-1-(1,3-thiazol-2-yl)ethyl]-2-methylcyclohexanecarboxylate (Intermediate 14).

DETAILED DESCRIPTION OF THE INVENTION

The present invention provides compounds of formula I:

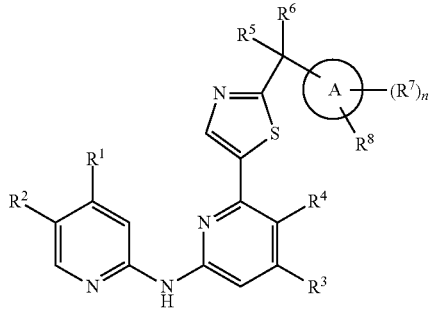

I or a pharmaceutically acceptable salt thereof,
wherein
A is a carbocycle, or
the moiety A-$(R^7)_n(R^8)$ represents

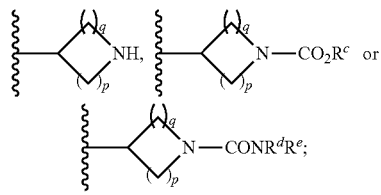

n is 0, 1, 2 or 3;
p and q are independently selected from 1, 2 and 3;
$R^1$ is $C_{1-4}$alkyl, $C_{1-4}$fluoroalkyl, $C_{3-6}$cycloalkyl or $C_{1-4}$alkoxy;
$R^2$ is H or halogen;
$R^3$ is H, halogen, $C_{1-4}$alkyl, $C_{1-4}$haloalkyl, $C_{3-6}$cycloalkyl or $C_{1-4}$ hydroxyalkyl;
$R^4$ is H or halogen;
$R^5$ is OH, $C_{1-4}$alkoxy, halogen, $NH_2$; or $N(H)(C_{1-4}$alkyl);
$R^6$ is H, $C_{1-4}$haloalkyl, $C_{3-6}$ cycloalkyl or $C_{1-4}$hydroxyalkyl; or
$R^7$ is selected from OH and $C_{1-4}$ alkyl;
$R^8$ is selected from $(CR^aR^b)_nCO_2R^c$, $CONR^dR^e$, tetrazolyl, OH, $CH_2OH$, oxo, CN, $NHCO_2R^f$ and $NHSO_2R^f$; with the proviso that $R^8$ and $C(R^5)(R^6)$ are not attached to the same ring carbon atom;
$R^a$ and $R^b$ are each independently selected from H and methyl;
$R^c$ is H or $C_{1-4}$ alkyl,
$R^d$ and $R^e$ are each independently selected from H and $C_{1-4}$alkyl; and
$R^f$ is $C_{1-4}$alkyl or benzyl.

In one group of formula I are compounds wherein the ring A is a carbocycle. In one subgroup thereof is selected from $C_{3-6}$ cycloalkyl. In one embodiment A is selected from cyclopropyl, cyclobutyl, cyclopentyl and cyclohexyl. In a second embodiment A is cyclohexyl.

In another group of formula I are compounds wherein $R^1$ is $C_{1-4}$alkyl or $C_{1-4}$ fluoroalkyl. In one subgroup thereof $R^1$ is $C_{1-3}$ alkyl, such as methyl, ethyl, n-propyl or isopropyl. In a second subset thereof $R^1$ is $C_{1-3}$ fluoroalkyl such as difluoromethyl or trifluoromethyl. In one embodiment $R^1$ is methyl. In a second embodiment $R^1$ is trifluoromethyl. In a third embodiment $R^1$ is cyclopropyl.

In another group of formula I are compounds wherein $R^2$ is H or F.

In another group of formula I are compounds wherein $R^3$ is $C_{1-4}$ alkyl, $C_{1-4}$ haloalkyl or $C_{3-6}$cycloalkyl. In one subgroup thereof $R^3$ is $C_{1-4}$alkyl, $C_{1-4}$fluoroalkyl or $C_{3-6}$ cycloalkyl. In one embodiment $R^3$ is selected from methyl, difluoromethyl and cyclopropyl. In a second embodiment $R^3$ is methyl.

In another group of formula I are compounds wherein $R^5$ is OH, $C_{1-4}$ alkoxy, halogen, or $NH_2$. In one embodiment $R^5$ is OH.

In another group of formula I are compounds wherein $R^6$ is H, $C_{1-4}$alkyl or $C_{1-4}$ haloalkyl. In one subgroup thereof $R^6$ is H, $C_{1-4}$ alkyl or $C_{1-4}$ fluoroalkyl. In another subgroup thereof $R^6$ is selected from H, $C_{1-3}$alkyl and fluoro-, difluoro- and trifluoromethyl. In one embodiment $R^6$ is methyl.

In another group of formula I are compounds wherein A is a carbocycle, and $R^8$ is selected from $(CR^aR^b)_nCO_2R^c$ and $C(O)NR^dR^e$. In one subgroup thereof $R^8$ is selected from $CO_2R^c$ and $C(O)NR^dR^e$. In one embodiment A is $C_{3-6}$ cycloalkyl and $R^8$ is $CO_2Re$. In a second embodiment A is $C_{3-6}$ cycloalkyl and $R^8$ is $C(O)NR^dR^e$.

In another group of formula I are compounds having the formula Ia:

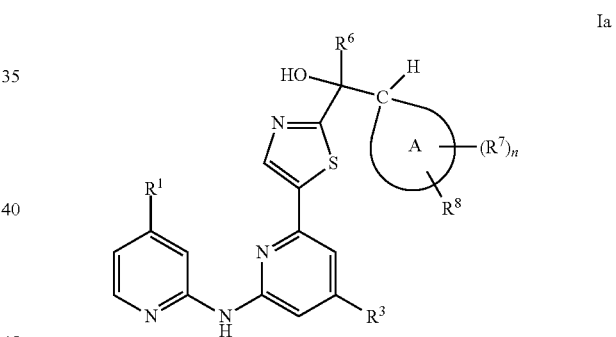

Ia or a pharmaceutically acceptable salt thereof,
wherein
A is a carbocycle;
n is 0, 1 or 2;
$R^1$ is $C_{1-4}$alkyl or $C_{1-4}$fluoroalkyl;
$R^3$ is H, $C_{1-4}$alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$alkyl;
$R^8$ is $CO_2Re$ or $CONR^dR^e$;
$R^c$ is H or $C_{1-4}$alkyl,
$R^d$ and $R^e$ are each independently selected from H and $C_{1-4}$alkyl.

In one group of formula Ia, $R^3$ is $C_{1-4}$alkyl, $C_{1-4}$haloalkyl or $C_{3-6}$cycloalkyl. In another group thereof, $R^3$ is H, $C_{1-4}$alkyl, $C_{1-4}$fluoroalkyl or $C_{3-6}$cycloalkyl. In another group, $R^3$ is H, methyl, difluoromethyl, and cyclopropyl. In one embodiment $R^3$ is H or methyl.

In another group of formula Ia, $R^6$ is H, $C_{1-4}$ alkyl, $C_{1-4}$ fluoroalkyl or $C_{3-4}$cycloalkyl.

In another group of formula Ia, $R^3$ is $C_{1-4}$alkyl, $C_{1-4}$haloalkyl or $C_{3-6}$cycloalkyl; and $R^6$ is H, $C_{1-4}$alkyl, or $C_{1-4}$haloalkyl.

In another group of formula I are compounds having the formula Ib:

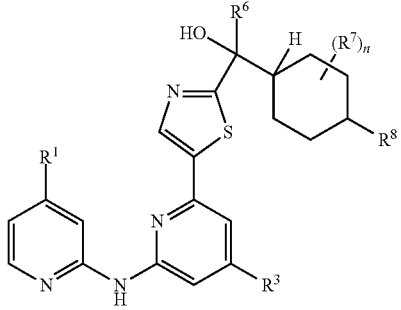

or a pharmaceutically acceptable salt thereof,
wherein
n is 0, 1 or 2;
$R^1$ is $C_{1-4}$alkyl or $C_{1-4}$fluoroalkyl;
$R^3$ is $C_{1-4}$ alkyl, $C_{1-4}$haloalkyl or $C_{3-6}$cycloalkyl;
$R^6$ is H, $C_{1-4}$alkyl or $C_{1-4}$haloalkyl;
$R^7$ is $C_{1-4}$ alkyl;
$R^8$ is $CO_2R^c$ or $CONR^dR^e$;
$R^c$ is H or $C_{1-4}$alkyl,
$R^d$ and $R^e$ are each independently selected from H and $C_{1-4}$alkyl.

In one group of formula Ib, $R^3$ is $C_{1-4}$alkyl, $C_{1-4}$haloalkyl or $C_{3-6}$cycloalkyl. In another group thereof, $R^3$ is H, $C_{1-4}$alkyl, $C_{1-4}$fluoroalkyl or $C_{3-6}$cycloalkyl. In another group, $R^3$ is H, methyl, difluoromethyl, and cyclopropyl. In one embodiment $R^3$ is H or methyl.

In another group of formula Ib, $R^6$ is H, $C_{1-4}$alkyl, $C_{1-4}$fluoroalkyl or $C_{3-4}$cycloalkyl.

In another group of formula Ib, $R^3$ is $C_{1-4}$alkyl, $C_{1-4}$haloalkyl or $C_{3-6}$cycloalkyl; and
$R^6$ is H, $C_{1-4}$ alkyl, or $C_{1-4}$ haloalkyl.

In certain embodiments of the compounds having the formula Ib, the moiety

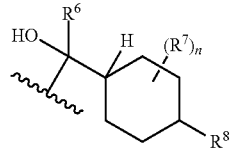

has the configuration

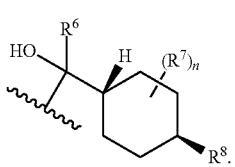

Representative compounds of the present invention are as follows, where each named compound is intended to encompass its individual isomers, mixtures thereof (including racemates and diastereomeric mixtures), as well as pharmaceutically acceptable salts thereof:

trans-4-[1-(5-{6-[(4-cyclopropylpyridin-2-yl)amino]-4-methylpyridin-2-yl}-1,3-thiazol-2-yl)-1-hydroxypropyl]cyclohexanecarboxylic acid;

trans-4-[1-(5-{6-[(4-cyclopropylpyridin-2-yl)amino]-4-methylpyridin-2-yl}-1,3-thiazol-2-yl)-1-hydroxypropyl]cyclohexanecarboxamide;

trans-4-[1-(5-{6-[(5-fluoro-4-methylpyridin-2-yl)amino]pyridin-2-yl}-1,3-thiazol-2-yl)-1-hydroxyethyl]cyclohexanecarboxylic acid;

trans-4-{1-hydroxy-1-[5-(6-{[4-(trifluoromethyl)pyridin-2-yl]amino}pyridin-2-yl)-1,3-thiazol-2-yl]ethyl}cyclohexanecarboxylic acid;

butyl trans-4-[1-(5-{6-[(5-fluoro-4-methylpyridin-2-yl)amino]-4-methylpyridin-2-yl}-1,3-thiazol-2-yl)-1-hydroxyethyl]cyclohexanecarboxylate;

trans-4-[1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid;

1-[5-(4-methyl-6-{[4-(trifluoromethyl)pyridin-2-yl]amino}pyridin-2-yl)-1,3-thiazol-2-yl]-1-(pyrrolidin-3-yl)ethanol; and 3-{1-hydroxy-1-[5-(4-methyl-6-{[4-(trifluoromethyl)pyridin-2-yl]amino}pyridin-2-yl)-1,3-thiazol-2-yl]ethyl}pyrrolidine-1-carboxamide.

trans-4-{1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid trans-4-[1-hydroxy-1-(5-{4-methyl-6-[(4-methylpyridin-2-yl)amino]pyridin-2-yl}-1,3-thiazol-2-yl)ethyl]cyclohexanecarboxylic acid butyl trans-4-[1-hydroxy-1-(5-{6-[(4-methoxypyridin-2-yl)amino]-4-methylpyridin-2-yl}-1,3-thiazol-2-yl)ethyl]cyclohexanecarboxylate trans-4-[1-hydroxy-1-(5-{6-[(4-methoxypyridin-2-yl)amino]-4-methylpyridin-2-yl}-1,3-thiazol-2-yl)ethyl]cyclohexanecarboxylic acid trans-4-{1-[5-(6-{[4-(difluoromethyl)pyridin-2-yl]amino}-4-methylpyridin-2-yl)-1,3-thiazol-2-yl]-1-hydroxyethyl}cyclohexanecarboxylic acid trans-4-[1-(5-{6-[(5-chloro-4-methylpyridin-2-yl)amino]-4-methylpyridin-2-yl}-1,3-thiazol-2-yl)-1-hydroxyethyl]cyclohexanecarboxylic acid butyl trans-4-[1-(5-{6-[(4-cyclopropylpyridin-2-yl)amino]-4-methylpyridin-2-yl}-1,3-thiazol-2-yl)-1-hydroxyethyl]cyclohexanecarboxylate trans-4-[1-(5-{6-[(4-cyclopropylpyridin-2-yl)amino]-4-methylpyridin-2-yl}-1,3-thiazol-2-yl)-1-hydroxyethyl]cyclohexanecarboxylic acid trans-4-{1-hydroxy-1-[5-(4-methyl-6-{[4-(propan-2-yl)pyridin-2-yl]amino}pyridin-2-yl)-1,3-thiazol-2-yl]ethyl}cyclohexanecarboxylic acid trans-4-[1-(5-{6-[(5-fluoro-4-methylpyridin-2-yl)amino]-4-methylpyridin-2-yl}-1,3-thiazol-2-yl)-1-hydroxyethyl]cyclohexanecarboxylic acid 3-{1-hydroxy-1-[5-(4-methyl-6-{[4-(trifluoromethyl)pyridin-2-yl]amino}pyridin-2-yl)-1,3-thiazol-2-yl]ethyl}cyclopentanecarboxylic acid trans-4-{1-hydroxy-1-[5-(4-methyl-6-{[4-(trifluoromethyl)pyridin-2-yl]amino}pyridin-2-yl)-1,3-thiazol-2-yl]propyl}cyclohexanecarboxylic acid trans-4-{cyclopropyl(hydroxy)[5-(4-methyl-6-{[4-(trifluoromethyl)pyridin-2-yl]amino}pyridin-2-yl)-1,3-thiazol-2-yl]methyl}cyclohexanecarboxylic acid trans-4-{2,2,2-trifluoro-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid trans-4-{1-hydroxy-1-[5-(4-methyl-6-{[4-(propan-2-yloxy)pyridin-2-yl]amino}pyridin-2-yl)-1,3-thiazol-2-yl]propyl}cyclohexanecarboxylic acid trans-4-{cyclopropyl(hydroxy)[5-(4-methyl-6-{[4-(propan-2-yloxy)pyridin-2-yl]amino}pyridin-2-yl)-1,3-thiazol-2-yl]methyl}cyclohexanecarboxylic acid trans-4-{2,2,2-trifluoro-1-hydroxy-1-[5-(4-methyl-6-{[4-(propan-2-yloxy)pyridin-2-yl]amino}pyridin-2-yl)-1,3-thiazol-2-yl]ethyl}cyclohexanecarboxylic acid methyl trans-4-{hydroxy[5-(4-methyl-6-{[4-(trifluoromethyl)pyridin-2-yl]amino}pyridin-2-yl)-1,3-thiazol-2-yl]methyl}cyclohexanecarboxylate trans-4-{hydroxy[5-(4-methyl-6-{[4-(trifluoromethyl)pyridin-2-yl]amino}pyridin-2-yl)-1,3-thiazol-2-yl]methyl}cyclohexanecarboxylic acid (1S,4R)-4-{1-hydroxy-1-[5-(4-methyl-6-{[4-(trifluoromethyl)pyridin-2-yl]amino}pyridin-2-yl)-1,3-thiazol-2-yl]ethyl}-2,2-dimethylcyclohexanecarboxylic acid (1S,4S)-4-{1-hydroxy-1-[5-(4-methyl-6-{[4-(trifluoromethyl)pyridin-2-yl]amino}pyridin-2-yl)-1,3-thiazol-2-yl]ethyl}-2,2-dimethylcyclohexanecarboxylic acid (1S,4S)-4-[1-hydroxy-1-(5-{4-methyl-6-[(4-methylpyridin-2-yl)amino]pyridin-2-yl}-1,3-thiazol-2-yl)ethyl]-2,2-dimethylcyclohexanecarboxylic acid (1S,4S)-4-[1-hydroxy-1-(5-{6-[(4-methoxypyridin-2-yl)amino]-4-methylpyridin-2-yl}-1,3-thiazol-2-yl)ethyl]-2,2-dimethylcyclohexanecarboxylic acid (1S,4S)-4-{1-[5-(6-{[4-(difluoromethyl)pyridin-2-yl]amino}-4-methylpyridin-2-yl)-1,3-thiazol-2-yl]-1-hydroxyethyl}-2,2-dimethylcyclohexanecarboxylic acid trans-4-[1-hydroxy-1-(5-{6-[(4-methylpyridin-2-yl)amino]pyridin-2-yl}-1,3-thiazol-2-yl)ethyl]cyclohexanecarboxylic acid trans-4-[1-hydroxy-1-(5-{6-[(4-methoxypyridin-2-yl)amino]pyridin-2-yl}-1,3-thiazol-2-yl)ethyl]cyclohexanecarboxylic acid trans-4-{1-[5-(6-{[4-(difluoromethyl)pyridin-2-yl]amino}pyridin-2-yl)-1,3-thiazol-2-yl]-1-hydroxyethyl}cyclohexanecarboxylic acid trans-4-{1-hydroxy-1-[5-(6-{[4-(propan-2-yl)pyridin-2-yl]amino}pyridin-2-yl)-1,3-thiazol-2-yl]ethyl}cyclohexanecarboxylic acid (1S,4S)-4-{1-hydroxy-1-[5-(6-{[4-(trifluoromethyl)pyridin-2-yl]amino}pyridin-2-yl)-1,3-thiazol-2-yl]ethyl}-2,2-dimethylcyclohexanecarboxylic acid (1S,4S)-4-[1-hydroxy-1-(5-{6-[(4-methylpyridin-2-yl)amino]pyridin-2-yl}-1,3-thiazol-2-yl)ethyl]-2,2-dimethylcyclohexanecarboxylic acid (1S,4S)-4-[1-hydroxy-1-(5-{6-[(4-methoxypyridin-2-yl)amino]pyridin-2-yl}-1,3-thiazol-2-yl)ethyl]-2,2-dimethylcyclohexanecarboxylic acid (1S,4S)-4-{1-[5-(6-{[4-(difluoromethyl)pyridin-2-yl]amino}pyridin-2-yl)-1,3-thiazol-2-yl]-1-hydroxyethyl)-2,2-dimethylcyclohexanecarboxylic acid trans-4-{1-[5-(4-chloro-6-{[4-(trifluoromethyl)pyridin-2-yl]amino}pyridin-2-yl)-1,3-thiazol-2-yl]-1-hydroxyethyl}cyclohexanecarboxylic acid trans-4-{1-[5-(4-(difluoromethyl)-6-{[4-(trifluoromethyl)pyridin-2-yl]amino}pyridin-2-yl)-1,3-thiazol-2-yl}-1-hydroxyethyl)cyclohexanecarboxylic acid trans-4-{1-[5-(4-cyclopropyl-6-[4-(trifluoromethyl)pyridin-2-yl]amino}pyridin-2-yl)-1,3-thiazol-2-yl]-1-hydroxyethyl}cyclohexanecarboxylic acid (4R)-4-{(1S)-1-hydroxy-1-[5-(4-methyl-6-{[4-(trifluoromethyl)pyridin-2-yl]amino}pyridin-2-yl)-1,3-thiazol-2-yl]ethyl}pyrrolidin-2-one (4R)-4-{(1R)-1-hydroxy-1-[5-(4-methyl-6-{[4-(trifluoromethyl)pyridin-2-yl]amino}pyridin-2-yl)-1,3-thiazol-2-yl]ethyl}pyrrolidin-2-one 4-{1-hydroxy-1-[5-(4-methyl-6-[4-(trifluoromethyl)pyridin-2-yl]amino}pyridin-2-yl)-1,3-thiazol-2-yl]ethyl)-2-methylcyclohexanecarboxylic acid In another embodiment, the compounds (including pharmaceutically acceptable salts thereof) are selected from the following compounds:

trans-4-[1-(5-{6-[(4-cyclopropylpyridin-2-yl)amino]-4-methylpyridin-2-yl}-1,3-thiazol-2-yl)-1-hydroxypropyl]cyclohexanecarboxylic acid;

trans-4-[1-(5-{6-[(4-cyclopropylpyridin-2-yl)amino]-4-methylpyridin-2-yl}-1,3-thiazol-2-yl)-1-hydroxypropyl]cyclohexanecarboxamide;

cis-4-{1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid;

trans-4-[1-(5-{6-[(5-fluoro-4-methylpyridin-2-yl)amino]pyridin-2-yl}-1,3-thiazol-2-yl)-1-hydroxyethyl]cyclohexanecarboxylic acid;

trans-4-{1-hydroxy-1-[5-(6-{[4-(trifluoromethyl)pyridin-2-yl]amino}pyridin-2-yl)-1,3-thiazol-2-yl]ethyl}cyclohexanecarboxylic acid;

butyl trans-4-[1-(5-{6-[(5-fluoro-4-methylpyridin-2-yl)amino]-4-methylpyridin-2-yl}-1,3-thiazol-2-yl)-1-hydroxyethyl]cyclohexanecarboxylate;

trans-4-[1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid;

1-[5-(4-methyl-6-{[4-(trifluoromethyl)pyridin-2-yl]amino}pyridin-2-yl)-1,3-thiazol-2-yl]-1-(pyrrolidin-3-yl)ethanol; and 3-{1-hydroxy-1-[5-(4-methyl-6-{[4-(trifluoromethyl)pyridin-2-yl]amino}pyridin-2-yl)-1,3-thiazol-2-yl]ethyl}pyrrolidine-1-carboxamide.

In another embodiment, the compounds (including pharmaceutically acceptable salts thereof) are selected from the following compounds:

trans-4-[(1R)-1-(5-{6-[(4-cyclopropylpyridin-2-yl)amino]-4-methylpyridin-2-yl}-1,3-thiazol-2-yl)-1-hydroxypropyl]cyclohexanecarboxylic acid;

trans-4-[(1S)-1-(5-{6-[(4-cyclopropylpyridin-2-yl)amino]-4-methylpyridin-2-yl}-1,3-thiazol-2-yl)-1-hydroxypropyl]cyclohexanecarboxylic acid;

trans-4-[(1R)-1-(5-{6-[(4-cyclopropylpyridin-2-yl)amino]-4-methylpyridin-2-yl}-1,3-thiazol-2-yl)-1-hydroxypropyl]cyclohexanecarboxamide;

trans-4-[(1S)-1-(5-{6-[(4-cyclopropylpyridin-2-yl)amino]-4-methylpyridin-2-yl}-1,3-thiazol-2-yl)-1-hydroxypropyl]cyclohexanecarboxamide;

trans-4-{(1R)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid;

trans-4-{(1S)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid;

trans-4-[(1R)-1-(5-{6-[(5-fluoro-4-methylpyridin-2-yl)amino]pyridin-2-yl}-1,3-thiazol-2-yl)-1-hydroxyethyl]cyclohexanecarboxylic acid;

trans-4-[(1S)-1-(5-{6-[(5-fluoro-4-methylpyridin-2-yl)amino]pyridin-2-yl}-1,3-thiazol-2-yl)-1-hydroxyethyl]cyclohexanecarboxylic acid;

trans-4-{(1R)-1-Hydroxy-1-[5-(6-{[4-(trifluoromethyl)pyridin-2-yl]amino}pyridin-2-yl)-1,3-thiazol-2-yl]ethyl}cyclohexanecarboxylic acid;

trans-4-{(1S)-1-Hydroxy-1-[5-(6-{[4-(trifluoromethyl)pyridin-2-yl]amino}pyridin-2-yl)-1,3-thiazol-2-yl]ethyl}cyclohexanecarboxylic acid;
trans-4-[(1R)-1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid; and
trans-4-[(1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid.

In the application various terms are as defined below, unless otherwise specified:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Carbocycle" refers to a non-aromatic saturated or partially unsaturated monocyclic ring in which all ring atoms are carbon, and the ring being isolated or fused (including ortho-fused, Spiro-fused and bridged) to one or two such ring or to a benzene ring. In the case of a polycyclic carbocycle, the attachment point may be on any ring. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-6}$ cycloalkyl" refers to a saturated ring having from 3 to 6 ring carbon atoms. Exemplary "cycloalkyl" groups useful in the present invention include, but are not limited to, cyclopropyl, cyclobutyl, cyclopentyl and cyclohexyl.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one $R^7$ substituents on the "A" ring, each substituent is independently selected at each occurrence, and each substituent can be the same or different from the other(s).

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HW and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula I or a salt, solvate or physiologically functional derivative thereof.

As used herein, the term "solvate" refers to a complex of variable stoichiometry formed by a solute (in this invention, a compound of formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula I may have the ability to crystallize in more than one form, a characteristic known as polymorphism, and it is understood that such polymorphic forms ("polymorphs") are within the scope of formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of formula I may contain asymmetric or chiral centers, and, therefore, exist in different stereoisomeric forms. It is intended that all stereoisomeric forms of the compounds of formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of formula I may be atropisomers (e.g., substituted biaryls) and are considered as part of this invention.

It is also noted that the compounds of formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula I can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of formula I.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula I can be prepared without undue experimentation by conventional techniques well known to those skilled in the art or by processes analogous to those described in the Schemes and Examples herein using appropriate isotopically-enriched reagents and/or intermediates The compounds of formula I and salts, solvates and physiologically functional derivatives thereof are believed to be inhibitors of Syk activity, and thus be potentially useful in the treatment of diseases and conditions associated with inappropriate Syk activity.

Compound of formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula I or a pharmaceutically acceptable salt, solvate, or a physiologically functional derivative thereof.

In a further embodiment, the present invention provides for the use of a compound of formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 3 g, preferably 1 mg to 700 mg, more preferably 5 mg to 100 mg of a compound of the formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (WAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihalerilb (Boehringer Ingelheim), Pulvinal® (Chiesi), Rotahaler® (GlaxoSmithKline), SkyeHaler™ or Certihaler™ (SkyePharma), Twisthaler® (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
|---|---|
| Compound of formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of formula I | 25 |
| Lactose Powder | 573.5 |
| Magnesium Stearate | 1.5 |
| | 600 |

| Inhalation Aerosol | Per dose |
|---|---|
| Compound of formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
|---|---|
| Compound of formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I for the treatment of diseases or conditions associated with inappropriate Syk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula I or a pharmaceutically acceptable salt or solvate thereof, or a physiologically functional derivative thereof, and the use of at least one other pharmaceutically active agent. The compound(s) of formula I and the other pharmaceutically active agent(s) may be administered together or separately and, when administered separately this may occur simultaneously or sequentially in any order. The amounts of the compound(s) of formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate), salmeterol or a pharmaceutically acceptable salt thereof (e.g., salmeterol xinafoate) and fluticasone propionate.

For the treatment of cancer a compound of formula I may be combined with one or more of an anticancer agent. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, fluoromethylene-2'-deoxycytidine, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-11, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl) methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU 182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refers to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, fluoromethylene-2'-deoxycytidine, N6-[4-deoxy-4-[N2-[2,4-tetradecadienoyl]glycylamino]-L-glycero-B-L-mannoheptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:

Biological Assay

Homogeneous Time-Resolved Fluorescence (HTRF) Assay for the Recombinant Human Syk Enzyme:

A recombinant GST-hSyk fusion protein was used to measure potency of compounds to inhibit human Syk activity. The recombinant human GST-Syk (Curia Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45 minutes at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on an EnVision (Perkin-Elmer) reader using a time-resolved fluorescence protocol. $IC_{50}$ was determined following 10-dose titration (10 µM to 0.508 nM) and four parameter logistic curve fitting using the Merck Assay Data Analyzer. The rhSyk activity ($IC_{50}$) is expressed as +++(100 nM or less), ++(between 100 and 1000 nM), +(between 1 and 10 µM). $IC_{50}$ values are also provided for the following representative compounds:

| Example No. | rhSyk (nM) |
| --- | --- |
| Example 1, Enantiomer 1 | 2.9 |
| Example 2, racemic mixture | 3.1 |
| Example 9, Enantiomer 1 | 278 |
| Example 10 | 0.1 |
| Example 11 | 0.5 |
| Example 14, Step 2 | 0.5 |
| Example 14-2 | 219 |
| Example 14-4 | 0.5 |
| Example 14-14 | 0.5 |
| Example 14-15 | 0.5 |
| Example 14-28 | 1.1 |
| Example 14-50 | 6 |

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of formula I. Those skilled in the art will recognize if a stereocenter exists in compounds of formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)=4-butyloxycarbonyl; BOP=(Benzotriazol-1-yloxy)-tris(dimethylamino)phosphonium hexafluorophosphate; DAST=(Diethylamino)sulfur trifluoride; dba=dibenzylideneacetone; DCE=1,2-dichloroethane; DCM=Dichloromethane; Dibal/Dibal-H=Diisobutylaluminum hydride; DIPEA/DIEA=Diisopropylethylamine; DMAP=N,N-dimethyl-aminopyridine; DME=1,2-dimethoxyethane; DMF=Dimethyl formamide; DMSO=Dimethyl-sulfoxide; Dppf=1,1'-Bis(diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl)uronium hexafluorophosphate; HMDS=Hexamethyldisilazane; HOBT=1-Hydroxybenzotriazole; IPA=Isopropyl alcohol; LDA=Lithium diisopropylamide; mCPBA=Meta-chloroperoxy-benzoic acid; Ms=Methanesulfonyl (mesyl); MTBE=Methyl t-butyl ether; NBS=N-bromo-succinimide; Ph phenyl; TBAF=t-butylammonium fluoride; TBDMS/TBS=t-butyl dimethylsilyl; TFA=Trifluoroacetic acid/trifluroacetate; THF=Tetrahydrofuran; TLC=Thin-layer chromatography; TMS=Trimethylsilyl; Ts=Toluenesulfonyl (tosyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

SCHEME 1

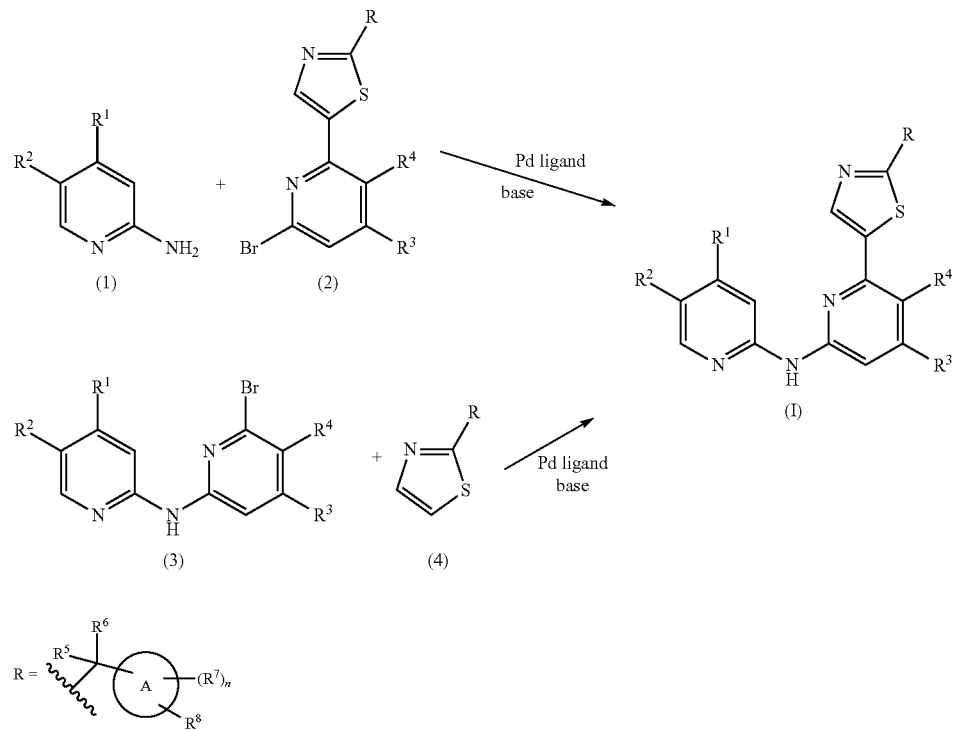

Compounds of formula I may be prepared by palladium-mediated coupling of substituted amino pyridines (1) with pyridyl thiazoles (2). Alternatively, compounds of formula I can also be obtained by reacting substituted aminobispyridines (3) with substituted thiazoles (4).

SCHEME 2

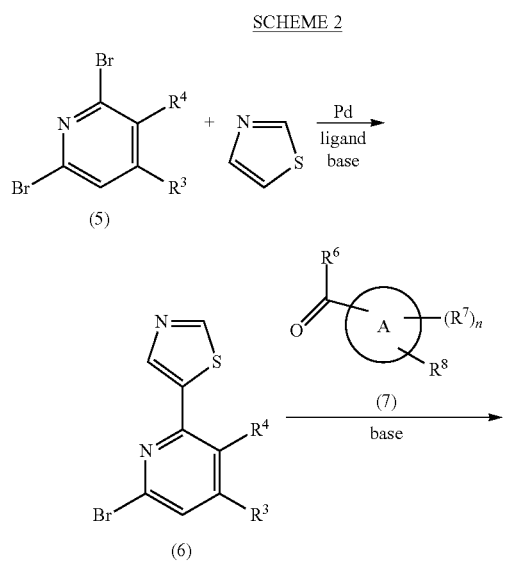

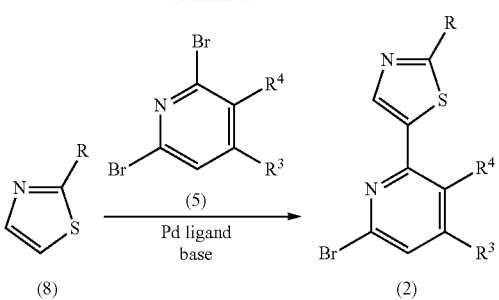

As depicted in scheme 3, compounds of formula (2) can also be prepared by first deprotonating thiazole with a strong base, such as LDA, and reacting the resultant species with an electrophile like (7) to yield substituted thiazole (8). Reaction of the thiazole (8) with a bis-halo pyridine (5) affords compounds of formula (2).

SCHEME 4

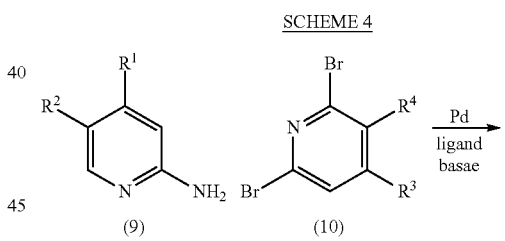

Compounds of formula (2) can be prepared by coupling a bis-halo pyridine of type (5) with thiazole using a palladium catalyst. The pyridyl thiazole (6) can be deprotonated with a strong base, such as LDA, and reacted with an electrophile like (7) to provide (2).

SCHEME 3

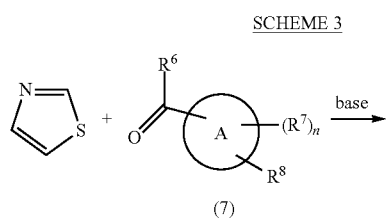

Aminobispyridines (3) can be synthesized according to scheme 4. Coupling of aminopyridines (9) with bis-halo pyridines (10) using a palladium catalyst provides compounds of formula (3).

Scheme 5

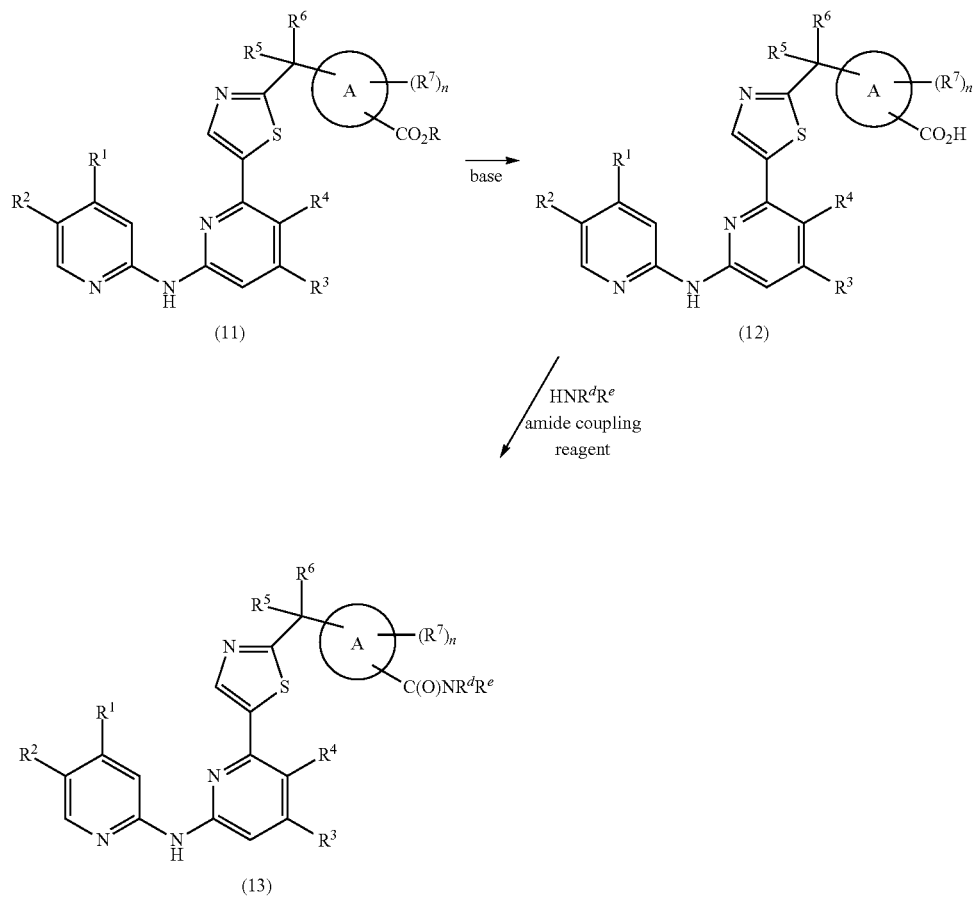

R = lower alkyl such as $C_{1-4}$alkyl

Some compounds of formula I are represented by carboxylic esters (11). Preparation of carboxylic acids (12) and amides (13) is demonstrated in Scheme 5. Carboxylic esters of type (11) can be hydrolyzed under basic conditions to yield carboxylic acids (12), which can be further derivatized using standard amide coupling reagents and amines to afford amides of formula (13).

SCHEME 6

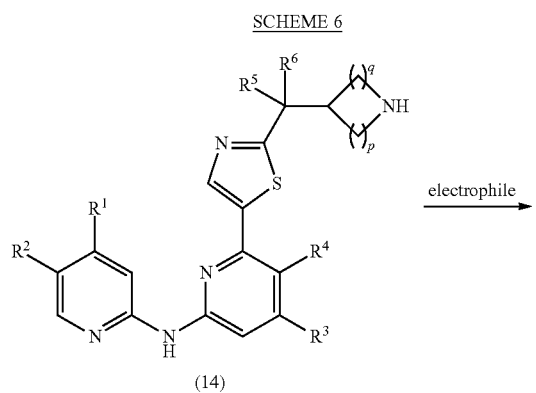

-continued

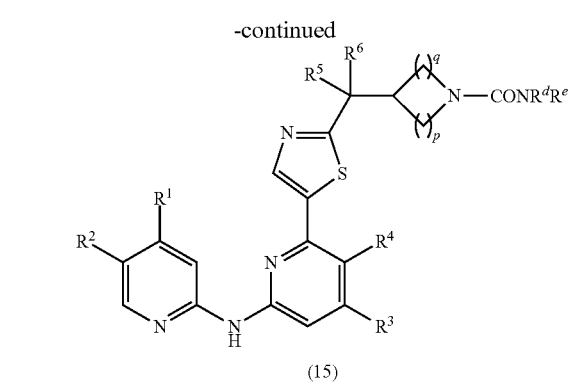

As depicted in Scheme 6, compounds of formula (15) can be prepared by reaction of amine (14) with electrophiles, such as potassium cyanate.

Compounds of formula I can be prepared according to the procedures described in the Schemes and Examples herein, using appropriate materials and are further exemplified by the following specific examples. The compounds exemplified are illustrative of the invention and are not, however, to be construed as limiting the scope of the invention in any manner.

The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

Intermediate 1. Butyl trans-4-acetylcyclohexanecarboxylate

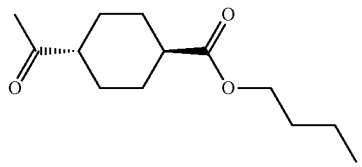 [SMILES: CCCCOC(=O)[C@H]1CC[C@H](C(C)=O)CC1]

To a vented and cooled solution (0° C.) under nitrogen of trans-4-(butoxycarbonyl)cyclohexanecarboxylic acid (*J. Chem. Soc., Perkin Trans.* 1, 1999, 20, 3023) (18.9 g, 83 mmol) in $CH_2Cl_2$ (150 mL) was added a catalytic amount of DMF (30 µL) followed by oxalyl chloride (7.97 mL, 91 mmol). The reaction mixture was then allowed to slowly warm to room temperature where it was stirred for 14 h at which point it was concentrated to a yellow oil and dried under vacuum for 3 h. The residue consisting primarily of butyl trans-4-(chlorocarbonyl)cyclohexanecarboxylate was diluted with THF (200 mL) and cooled in an ice bath. To this solution was added $PdCl_2(dppf)$-$CH_2Cl_2$ (3.38 g, 4.14 mmol) followed by dimethyl zinc (2 M in $PhCH_3$, 29 mL, 58 mmol) at such a rate that the internal temperature did not exceed 15° C. The cooling bath was then removed and after 2 h of stirring at room temperature the reaction mixture was re-cooled to 0° C. where it was diluted carefully with $H_2O$. After the initial exotherm had subsided, sufficient 1N HCl and EtOAc were introduced such that a homogenous biphasic mixture formed. The layers were separated, the organic washed a second time with $H_2O$ then dried with $MgSO_4$, filtered and concentrated in vacuo. The crude residue was absorbed on silica and purified by flash chromatography to afford butyl trans-4-acetylcyclohexanecarboxylate as a non-viscous orange oil. MS ESI calc'd. for $C_{13}H_{23}O_3$ $[M+H]^+$ 227. found 227. $^1$H NMR (500 MHz, $CDCl_3$) δ 4.06 (t, J=6.6 Hz, 2H), 2.37-2.29 (m, 1H), 2.28-2.20 (m, 1H), 2.14 (s, 3H), 2.11-2.02 (m, 2H), 1.99 (d, J=13.8 Hz, 2H), 1.66-1.55 (m, 2H), 1.51-1.40 (m, 2H), 1.39-1.29 (m, 4H), 0.93 (t, J=7.4 Hz, 3H).

Intermediate 2. Butyl trans-4-[(1R)-1-hydroxy-1-(1,3-thiazol-2-yl)ethyl]cyclohexanecarboxylate and butyl trans-4-[(1S)-1-hydroxy-1-(1,3-thiazol-2-yl)ethyl]cyclohexanecarboxylate

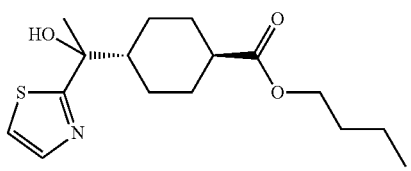 [SMILES: CCCCOC(=O)[C@H]1CC[C@H](C(C)(O)c2nccs2)CC1]

To a cooled (0° C.) flask under nitrogen containing iPrMgCl—LiCl (1.3 M in THF, 55.2 mL, 71.8 mmol) was added thiazole (5.10 mL, 71.8 mmol) keeping the internal temperature <10° C. The resulting heterogenous mixture was warmed to RT where it was stirred for 10 min then re-cooled to −20° C. Then, a solution of butyl trans-4-acetylcyclohexanecarboxylate (12.5 g, 55.2 mmol) in THF (20+5 mL) was added via syringe. The cooling bath was then removed and the reaction mixture warmed slowly to 10° C. during which time it was observed to nearly completely homogenize. After 40 min, saturated aqueous $NH_4Cl$ followed by EtOAc were added and the layers separated, the organics dried over $MgSO_4$, filtered and concentrated in vacuo. The crude residue was absorbed on silica and purified by flash chromatography to afford butyl trans-4-[1-hydroxy-1-(1,3-thiazol-2-yl)ethyl]cyclohexanecarboxylate as a light yellow oil. The enantiomers were separated by chiral SFC (Chiral Technology AZ-H, 2.1×25 cm, 5 uM, 45/55 MeOH/$CO_2$, Flow Rate: 80 mL/min, 6 min run time, WL: 220 nm) Elution was observed at 2.98 min and 4.14 min. Pooled fractions of each peak were separately concentrated under reduced pressure.

Peak 1 (retention time=2.98 min): MS ESI calc'd. for $C_{16}H_{25}NO_3S$ $[M+H]^+$ 312. found 312. $^1$H NMR (500 MHz, DMSO-$d_6$) δ 7.67 (d, J=2.9, 1H), 7.51 (d, J=2.9, 1H), 5.73 (s, 1H), 3.95 (t, J=6.5, 2H), 2.16-2.01 (m, 1H), 1.95-1.74 (m, 3H), 1.62 (t, J=11.1, 1H), 1.54-1.34 (m, 6H), 1.34-1.08 (m, 5H), 1.06-0.91 (m, 1H), 0.85 (t, J=7.3, 3H).

Peak 2 (retention time=4.14 min) MS ESI calc'd. for $C_{16}H_{25}NO_3S$ $[M+H]^+$ 312. found 312. $^1$H NMR (500 MHz, DMSO-$d_6$) δ 7.67 (d, J=2.9, 1H), 7.51 (d, J=2.9, 1H), 5.73 (s, 1H), 3.95 (t, J=6.5, 2H), 2.16-2.01 (m, 1H), 1.95-1.74 (m, 3H), 1.62 (t, J=11.1, 1H), 1.54-1.34 (m, 6H), 1.34-1.08 (m, 5H), 1.06-0.91 (m, 1H), 0.85 (t, J=7.3, 3H).

Intermediate 3. 6-Bromo-N-(4-cyclopropylpyridin-2-yl)-4-methylpyridin-2-amine

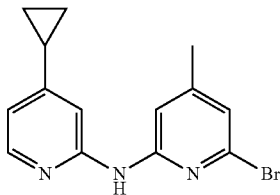 [SMILES: Cc1cc(Br)nc(Nc2cc(C3CC3)ccn2)c1]

A dry round bottomed flask was charged with 2-amino-4-cyclopropylpyridine (5.00 g, 31.7 mmol) and 2,6-dibromo-4-methylpyridine (7.95 g, 31.7 mmol). The reaction vessel was placed under an atmosphere of nitrogen (3× vacuum/$N_2$ cycle), then 1,4-dioxane (100 mL) was added and the mixture was degassed with a steady stream of nitrogen for 30 minutes. Sodium tert-butoxide (3.35 g, 34.8 mmol) and 1,1'-bis(di-tert-butylphosphino)ferrocene palladium dichloride (0.49 g, 0.75 mmol) were added to the reaction flask, then the reaction was stirred at room temperature for 15 minutes then heated to 50° C. for five hours. After cooling to room temperature for 14 hours, the resulting reaction mixture was poured into water (200 mL) and extracted with ethyl acetate (2×100 mL). The combined organic layers were further washed with water and brine (200 mL portions). The organic phase was dried over sodium sulfate, filtered, and concentrated under reduced pressure to yield an oil. The crude product was purified by silica gel chromatography (0-30% ethyl acetate/hexanes) to give the title compound as a brown solid. $^1$H NMR (600 MHz, DMSO-$d_6$) δ 9.80 (s, 1H), 8.06 (d, J=5.3 Hz, 1H), 7.70 (s, 1H), 7.23 (s, 1H), 6.92 (s, 1H), 6.61 (dd, J=1.4, 5.3 Hz, 1H), 2.25 (s, 3H), 1.91-1.78 (m, 1H), 1.09-0.98 (m, 2H), 0.82-0.66 (m, 2H).

Intermediate 4. Butyl trans-4-{1(R)-[5-(6-bromopyridin-2-yl)-1,3-thiazol-2-yl]-1-hydroxyethyl}cyclohexanecarboxylate and butyl trans-4-{1(S)-[5-(6-bromopyridin-2-yl)-1,3-thiazol-2-yl]-1-hydroxyethyl}cyclohexanecarboxylate

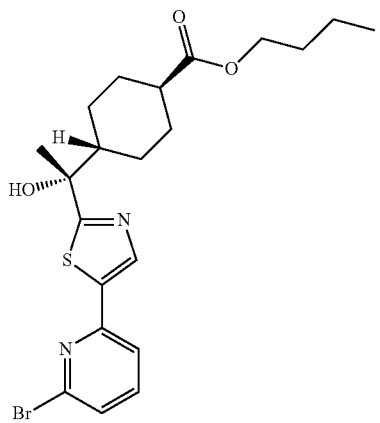

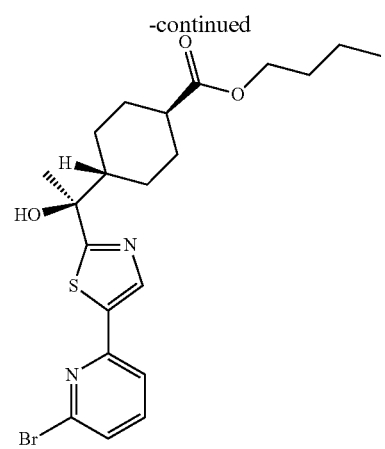

Step 1:

A suspension of 2,6-dibromopyridine (11.13 g, 47.0 mmol), pivalic acid (0.545 mL, 4.70 mmol), potassium carbonate (6.49 g, 47.0 mmol) in N,N-dimethylacetamide (45 mL) was deoxygenated by bubbling argon through it for 20 minutes. Thiazole (1.681 mL, 23.49 mmol) and tetrakis(triphenylphosphine)palladium(0) (1.086 g, 0.940 mmol) were added, the flask was sealed, and the reaction mixture was heated to 115° C. for 18 hours. The reaction mixture was cooled to room temperature and then diluted with water (50 mL), ethyl acetate (50 mL), and diethyl ether (50 mL). The layers were separated and then the organic layer was washed with water (2×50 mL), saturated aqueous sodium bicarbonate solution (25 mL), and brine (50 mL) The organic layer was dried over sodium sulfate, filtered, and concentrated under reduced pressure. The residue was purified by chromatography on silica gel (10-60% ethyl acetate/hexanes) to provide 2-bromo-6-(1,3-thiazol-5-yl)pyridine. MS ESI calc'd. for $C_8H_5BrN_2S$ [M+H]$^+$ 241 and 243. found 241 and 243. $^1$H NMR (500 MHz, DMSO-$d_6$) δ 9.19 (s, 1H), 8.64 (s, 1H), 8.06 (d, J=7.6 Hz, 1H), 7.83 (t, J=7.8 Hz, 1H), 7.58 (d, J=7.8 Hz, 1H).

Step 2:

To a solution of 2-bromo-6-(1,3-thiazol-5-yl)pyridine (457 mg, 1.895 mmol) in tetrahydrofuran (20 mL) at −78° C. was added lithium diisopropyl amide (1.8 M in tetrahydrofuran/heptane/ethylbenzene, 1.106 mmol, 1.990 mmol) over three minutes. After 30 minutes, a solution of butyl trans-4-acetyl-cyclohexanecarboxylate (450 mg, 1.990 mmol) in tetrahydrofuran (3 mL) was added to the reaction mixture. After an additional 70 minutes, a saturated aqueous ammonium chloride solution (10 mL) was added. Then, the reaction mixture was allowed to warm to room temperature before being diluted with ethyl acetate (50 mL), water (2 mL), and saturated aqueous ammonium chloride solution (10 mL). The layers were separated and the organic layer was sequentially washed with saturated aqueous sodium bicarbonate solution and brine, dried over sodium sulfate, filtered, and concentrated under reduced pressure. The residue was purified by chromatography on silica gel (0-20% ethyl acetate/dichloromethane) to give butyl trans-4-{1-[5-(6-bromopyridin-2-yl)-1,3-thiazol-2-yl]-1-hydroxyethyl}cyclohexanecarboxylate. MS ESI calc'd. for $C_{21}H_{27}BrN_2O_3S$ [M+H]$^+$ 467 and 469. found 467 and 469. Two enantiomers were separated by chiral super critical fluid chromatography (Chiral Technology IC-H, 2.1×25 cm, 5 uM, 70/30 ethanol/$CO_2$, Flow Rate: 70 mL/min, 6 min run time, WL: 220 nm) Elution was observed at 3.98 min and 4.76 min. Pooled fractions of each peak were concentrated under reduced pressure.

Enantiomer 1 (retention time=3.98 min): $^1$H NMR (500 MHz, CDCl$_3$) δ 8.12 (s, 1H), 7.61-7.51 (m, 2H), 7.37 (dd, J=2.7, 5.9 Hz, 1H), 4.04 (t, J=6.6 Hz, 2H), 3.00 (s, 1H), 2.22-2.16 (m, 1H), 2.08-2.01 (m, 1H), 1.99 (d, J=13.4 Hz, 2H), 1.83-1.76 (m, 1H), 1.62-1.56 (m, 3H), 1.61 (s, 3H), 144-1.34 (m, 4H), 1.32-1.24 (m, 1H), 1.22-1.15 (m, 1H), 0.92 (t, J=7.4 Hz, 3H). Enantiomer 2 (retention time=4.76 min): $^1$H NMR (500 MHz, CDCl$_3$) δ 8.12 (s, 1H), 7.61-7.51 (m, 2H), 7.37 (dd, J=2.7, 5.9 Hz, 1H), 4.04 (t, J=6.6 Hz, 2H), 2.99 (s, 1H), 2.25-2.17 (m, 1H), 2.08-2.02 (m, 1H), 1.99 (d, J=12.8 Hz, 2H), 1.82-1.75 (m, 1H), 1.63 (s, 3H), 1.62-1.56 (m, 3H), 1.43 (m, 1H), 1.40-1.24 (m, 3H), 1.30-1.24 (m, 1H), 1.21-1.15 (m, 1H), 0.92 (t, J=7.4 Hz, 3H).

Intermediate 5. 6-bromo-4-methyl-N-[4-(trifluoromethyl)pyridine-2-yl]pyridine-2-amine

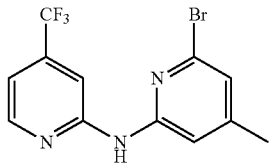 [SMILES: Cc1cc(Br)nc(Nc2cc(C(F)(F)F)ccn2)c1]

Sodium tert-butoxide (5.87 g, 61.1 mmol) and 1,1'-bis(di-tert-butylphosphino)ferrocene palladium dichloride (0.905 g, 1.4 mmol) were added to a solution of 2,6-dibromo-4-methyl pyridine (13.9 g, 55.5 mmol) and 2-amino-4-trifluoromethyl pyridine (9.0 g, 55.5 mmol) in nitrogen sparged dioxane (180 mL). The slurry was evacuated and refilled with nitrogen. The mixture was stirred at 25° C. for 15 minutes and then heated to 75° C. for 12 hours. The reaction mixture was cooled to 25° C., water (20 mL) was added, and the mixture was extracted with ethyl acetate (2×200 mL). The combined extracts were dried over sodium sulfate, filtered, concentrated under reduced pressure. The residue was purified by column chromatography on silica gel to afford 6-bromo-4-methyl-N-[4-(trifluoromethyl)pyridine-2-yl]pyridine-2-amine as a white solid. MS ESI calc'd. for $C_{12}H_{10}BrF_3N_3[M+H]^+$ 332 and 334. found 332 and 334. $^1$H NMR (600 MHz, DMSO-d$_6$) δ 10.40 (s, 1H), 8.46 (d, J=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following table were prepared according to the method described for Intermediate 5.

| Interm. | Structure | IUPAC Name | Exact Mass [M + H]+ | [M + H]+ Observed |
|---|---|---|---|---|
| 5.2 | 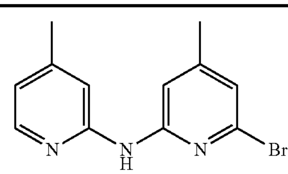 | 6-bromo-4-methyl-N-(4-methylpyridin-2-yl)pyridin-2-amine | 278 | 278, 280 |
| 5.3 | 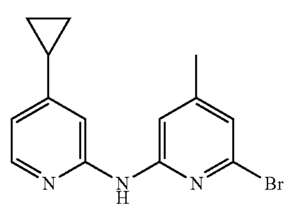 [SMILES: Cc1cc(Br)nc(Nc2cc(C3CC3)ccn2)c1] | 6-bromo-N-(4-cyclopropylpyridin-2-yl)-4-methylpyridin-2-amine | 304 | 304, 306 |
| 5.4 | 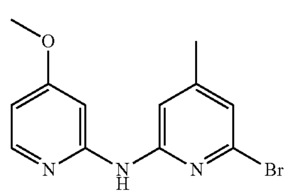 [SMILES: COc1ccnc(Nc2cc(C)cc(Br)n2)c1] | 6-bromo-N-(4-methoxypyridin-2-yl)4-methylpyridin-2-amine | 294 | 294, 296 |
| 5.5 | 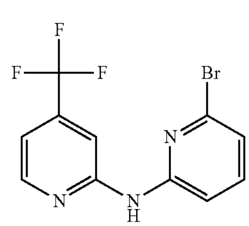 [SMILES: FC(F)(F)c1ccnc(Nc2cccc(Br)n2)c1] | N-(6-bromopyridin-2-yl)-4-(trifluoromethyl)pyridin-2-amine | 318 | 318, 320 |

| Interm. | Structure | IUPAC Name | Exact Mass [M + H]+ | [M + H]+ Observed |
|---|---|---|---|---|
| 5.6 | 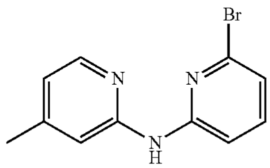 | N-(6-bromopyridin-2-yl)-4-methylpyridin-2-amine | 264 | 264, 266 |
| 5.7 | 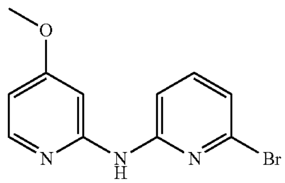 [SMILES: COc1ccnc(Nc2cccc(Br)n2)c1] | N-(6-bromopyridin-2-yl)-4-methoxypyridin-2-amine | 280 | 280, 282 |
| 5.8 | 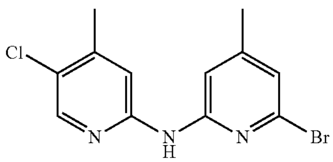 [SMILES: Cc1cc(Br)nc(Nc2cc(C)c(Cl)cn2)c1] | N-(6-bromo-4-methylpyridin-2-yl)-5-chloro-4-methylpyridin-2-amine | 312 | 312, 314 |
| 5.9 | 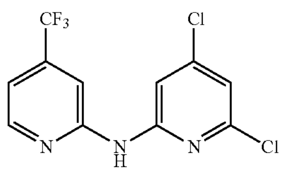 [SMILES: FC(F)(F)c1ccnc(Nc2cc(Cl)cc(Cl)n2)c1] | 4,6-dichloro-N-[4-(trifluoromethyl)pyridin-2-yl]pyridin-2-amine | 308 | 308 |
| 5.10 | 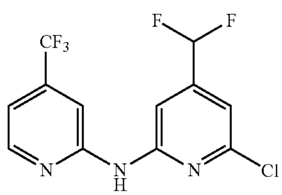 [SMILES: FC(F)c1cc(Cl)nc(Nc2cc(C(F)(F)F)ccn2)c1] | 6-chloro-4-(difluoromethyl)-N-[4-(trifluoromethyl)pyridin-2-yl]pyridin-2-amine | 324 | 324 |

Intermediate 6. 2,6-Dichloro-4-cyclopropylpyridine

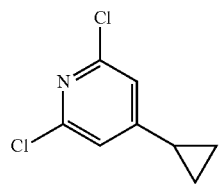 [SMILES: Clc1cc(C2CC2)cc(Cl)n1]

Cyclopropylzinc bromide (0.5 M in tetrahydrofuran, 15 mL, 7.3 mmol) was added to a mixture of 2,6-dichloro-4-iodopyridine (1.0 g, 3.65 mmol) and tetrakis(triphenylphosphine)palladium(0) (211 mg, 0.182 mmol) in anhydrous tetrahydrofuran (10 mL) at 0° C. After being stirred at room temperature for 4 hours, the reaction mixture was filtered, and the filtrate was concentrated under reduced pressure. The residue was purified by column chromatography on silica gel (petroleum ether: ethyl acetate=100:1) to provide 2,6-dichloro-4-cyclopropylpyridine. MS ESI calc'd. for $C_8H_8Cl_2N$ [M+H]+ 188. found 188. $^1$H NMR: (400 MHz, CDCl$_3$) δ 6.89 (s, 2H), 1.87-1.80 (m, 1H), 1.18-1.13 (m, 2H), 0.84-0.80 (m, 2H).

Intermediate 7. 6-Bromo-N-[4-(difluoromethyl)pyridin-2-yl]-4-methylpyridin-2-amine

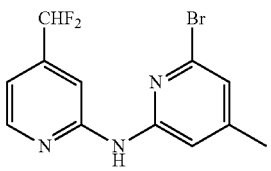 [SMILES: Cc1cc(Br)nc(Nc2cc(C(F)F)ccn2)c1]

Potassium t-butoxide (1.0 M in THF, 198 mL, 198 mmol) was added to a solution of 6-bromo-4-methyl pyridine-2-amine (37 g, 198 mmol) and 2-chloro-4-(difluoromethyl)pyridine (42.1 g, 257 mmol) in THF (60 mL) at 0° C. The resulting mixture was heated to reflux for 30 minutes then cooled to 0° C., and a second portion of potassium t-butoxide (1.0 M in THF, 80 mL, 80 mmol) was added. The mixture was again heated to reflux for 30 minutes, cooled to 0° C., and a third portion of potassium t-butoxide (1.0 M in THF, 80 mL, 80 mmol) was added. The mixture was again heated to reflux for 30 minutes. After cooling to 0° C., a fourth portion of potassium t-butoxide (1.0 M in THF, 20 mL, 20 mmol) was added. Upon refluxing for 30 minutes, the reaction was allowed to cool to room temperature, then diluted with saturated aqueous NH₄Cl (500 mL) and diluted with DCM (500 mL). The layers were separated, and the aqueous layer was extracted a second time with DCM (500 mL). The combined organic layers were dried with Na₂SO₄, filtered through a pad of CELITE (150 g), and concentrated in vacuo. The residue was triturated with DCM (100 mL), filtered, and washed with hexanes (2×50 mL) to afford one portion of 6-bromo-N-[4-(difluoromethyl)pyridin-2-yl]-4-methylpyridin-2-amine. The filtrate was concentrated, absorbed on silica gel and purified via silica gel column chromatography (EtOAc/Hex) to afford a second portion of 6-bromo-N-[4-(difluoromethyl)pyridin-2-yl]-4-methylpyridin-2-amine. MS ESI calc'd. for $C_{12}H_{11}BrF_2N_3$ $[M+H]^+$ 314 and 316. found 314 and 316. $^1H$ NMR (600 MHz, DMSO-$d_6$) δ 10.20 (s, 1H), 8.35 (d, f=5.1 Hz, 1H), 7.69 (s, 1H), 7.64 (s, 1H), 7.01 (d, J=5.1 Hz, 1H), 6.96 (t, J=22.3 Hz, 1H), 6.95 (s, 1H), 2.24 (s, 3H).

The intermediates in the following table were prepared according to the method described for Intermediate 7.

Intermediate 8. Methyl trans-4-[cyclopropyl(hydroxy)1,3-thiazol-2-ylmethyl]cyclohexanecarboxylate

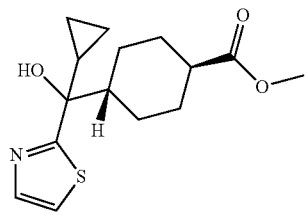

Step 1:
To a solution of trans-4-(methoxycarbonyl)cyclohexanecarboxylic acid (500 mg, 2.69 mmol) in dichloromethane (3 mL) at 0° C. was added oxalyl chloride (0.26 mL, 2.95 mmol) dropwise. The solution was stirred at 0° C. for 30 min and then allowed to warm to room temperature and stirred for one hour. The solution was then cooled back to 0° C. and 2-(trimethylsilyl)-1,3-thiazole (0.63 mL, 4.03 mmol) was added. The solution was allowed to warm to room temperature and then stirred for one hour. The solution was then poured into cold saturated sodium bicarbonate and then diluted with dichloromethane. The organic phase was separated, dried over magnesium sulfate, filtered and concentrated in vacuo. The crude product was purified by silica gel chromatography (0-30% ethyl acetate/hexanes) to provide methyl trans-4-(1,3-thia-

| Interm. | Structure | IUPAC Name | Exact Mass [M + H]+ | [M + H]+ Observed |
|---|---|---|---|---|
| 7.2 | 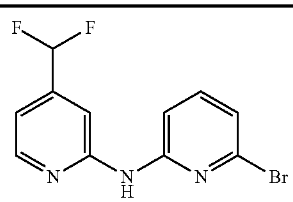 | N-(6-bromopyridin-2-yl)-4-(difluoromethyl)pyridin-2-amine | 300 | 300, 302 |
| 7.3 | 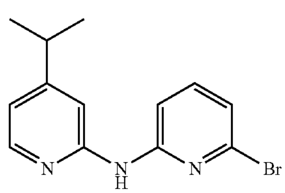 [SMILES: CC(C)c1ccnc(Nc2cccc(Br)n2)c1] | N-(6-bromopyridin-2-yl)-4-(propan-2-yl)pyridin-2-amine | 292 | 292, 294 |
| 7.4 | 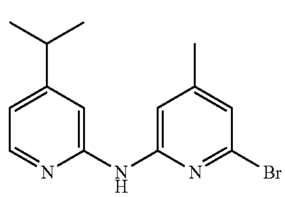 [SMILES: Cc1cc(Br)nc(Nc2cc(C(C)C)ccn2)c1] | 6-bromo-4-methyl-N-[4-(propan-2-yl)pyridin-2-yl]pyridin-2-amine | 306 | 306, 308 |
| 7.5 | | 6-chloro-4-cyclopropyl-N-[4-(trifluoromethyl)pyridin-2-yl]pyridin-2-amine | 314 | 314 | zol-2-ylcarbonyl)cyclohexanecarboxylate. MS ESI calc'd. for $C_{12}H_{16}NO_3S$ [M+H]$^+$ 254. found 254. $^1$H NMR (500 MHz, CDCl$_3$) δ 8.01 (dd, J=1.6, 2.9 Hz, 1H), 7.67 (dd, J=1.7, 2.9 Hz, 1H), 3.77-3.67 (m, 3H), 3.62 (t, J=11.1 Hz, 1H), 2.35 (t, J=10.4 Hz, 1H), 2.18-2.06 (m, 4H), 1.68-1.48 (m, 4H).

Step 2:

To a solution of methyl trans-4-(1,3-thiazol-2-ylcarbonyl)cyclohexanecarboxylate (2.59 g, 10.22 mmol) in THF (10 mL) at −78° C. was added cyclopropylmagnesium bromide (0.5 M in THF, 24 mL, 12.00 mmol) and the solution was stirred at this temperature for three hours. The solution was then allowed to warm for 15 minutes and then quenched with aqueous ammonium chloride. The solution was diluted with dichloromethane and the organic layer was separated, dried over magnesium sulfate, filtered and concentrated in vacuo. The crude product was purified by silica gel chromatography (0-30% ethyl acetate/hexanes. The product was further purified by reverse phase chromatography (25-100% acetonitrile/water with 0.1% TFA modifier) to afford methyl trans-4-[cyclopropyl(hydroxy)1,3-thiazol-2-ylmethyl]cyclohexanecarboxylate. MS ESI calc'd. for $C_{15}H_{22}NO_3S$ [M+H]$^+$ 296. found 296. $^1$H NMR (500 MHz, CDCl$_3$) δ 7.77 (d, J=3.4 Hz, 1H), 7.37 (d, J=3.4 Hz, 1H), 3.65 (s, 3H), 2.28-2.17 (m, 1H), 2.13-2.02 (m, 3H), 2.01-1.90 (m, 2H), 1.56-1.48 (m, 1H), 1.48-1.39 (m, 1H), 1.39-1.32 (m, 1H), 1.33-1.19 (m, 3H), 0.75-0.62 (m, 1H), 0.61-0.50 (m, 1H), 0.42-0.25 (m, 2H).

Intermediate 9. methyl trans-4-[2,2,2-trifluoro-1-hydroxy-1-(1,3-thiazol-2-yl)ethyl]cyclohexanecarboxylate

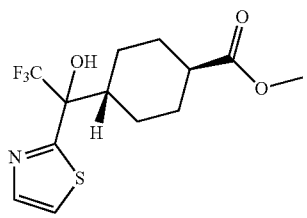 [SMILES: COC(=O)[C@H]1CC[C@H](C(O)(c2nccs2)C(F)(F)F)CC1]

To the solution of methyl trans-4-(thiazole-2-carbonyl)cyclohexanecarboxylate (1.1 g, 4.34 mmol) in THF (20 mL) at 0° C. was added trifluoromethyltrimethylsilane (1.286 mL, 8.68 mmol). Tetrabutylammonium fluoride trihydrate (1M in THF, 17.37 mL, 17.37 mmol) was added slowly maintaining the temperature at 0° C. The reaction was allowed to stir for 1 hr and then water (30 mL) and ethyl acetate (30 mL) was added to quench the reaction. The organic layer was removed, washed with brine (20 mL), dried over sodium sulfate, filtered and concentrated under reduced pressure. The residue was purified by chromatography on silica gel (0-20% ethyl acetate in hexane) to afford methyl trans-4-[2,2,2-trifluoro-1-hydroxy-1-(1,3-thiazol-2-yl)ethyl]cyclohexanecarboxylate. MS ESI calcd. for $C_{13}H_{17}F_3NO_3S$ [M+H]$^+$ 324. found 324. $^1$H NMR (500 MHz, CDCl$_3$) δ 7.79 (d, J=3.2 Hz, 1H), 7.49 (d, J=3.2 Hz, 1H), 4.77 (s, 1H), 3.65 (s, 3H), 2.40 (m, 1H), 2.30-1.90 (m, 3H), 1.50-1.20 (m, 6H).

Intermediate 10 Methyl trans-4-[hydroxy(1,3-thiazol-2-yl)methyl]cyclohexanecarboxylate

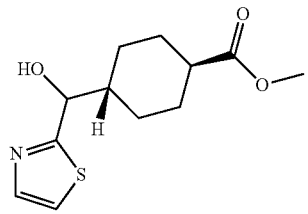 [SMILES: COC(=O)[C@H]1CC[C@H](C(O)c2nccs2)CC1]

To a solution of methyl trans-4-(1,3-thiazol-2-ylcarbonyl)cyclohexanecarboxylate (500 mg, 1.97 mmol) in methanol (20 mL) was added sodium borohydride (224 mg, 5.92 mmol) and the solution was stirred for one hour. The solution was then diluted with ethyl acetate and water. The organic layer was separated, dried over magnesium sulfate, filtered and concentrated in vacuo. The crude product was purified by silica gel chromatography to afford methyl trans-4-[hydroxy(1,3-thiazol-2-yl)methyl]cyclohexanecarboxylate. MS ESI calc'd. for $C_{12}H_{18}NO_3S$ [M+H]$^+$ 256. found 256. $^1$H NMR (500 MHz, DMSO-d$_6$) δ 7.70 (d, J=3.2 Hz, 1H), 7.58 (d, J=3.2 Hz, 1H), 6.10 (d, J=5.2 Hz, 1H), 4.59 (t, J=5.1 Hz, 1H), 3.54 (s, 3H), 2.21-2.11 (m, 1H), 1.92-1.83 (m, 2H), 1.75-1.64 (m, 1H), 1.64-1.53 (m, 2H), 1.33-1.11 (m, 4H).

Intermediate 11. (1S,3R)-methyl 3-(thiazole-2-carbonyl)cyclopentanecarboxylate(1S,3R)-methyl 3-(thiazole-2-carbonyl)cyclopentanecarboxylate

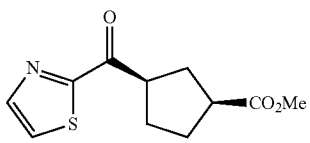 [SMILES: COC(=O)[C@H]1CC[C@@H](C(=O)c2nccs2)C1]

To a solution of (1R,3S)-3-(methoxycarbonyl)cyclopentanecarboxylic acid (130 mg, 0.76 mmol) in dichloromethane (3 mL) was added DMF (5.85 μL, 0.08 mmol). The solution was cooled to 0° C. oxalyl chloride (73.0 μL, 0.83 mmol) was added. The mixture was stirred at 0° C. for 30 minutes and then allowed to warm to room temperature for one hour. The reaction was re-cooled to 0° C., 2-(trimethylsilyl)thiazole (178.0 mL, 1.13 mmol) was added and the mixture was stirred at room temperature for two hours. The mixture was diluted with dichloromethane and washed with saturated sodium bicarbonate. The organic layer was separated, dried over magnesium sulfate, filtered and concentrated in vacuo. The residue was purified by column chromatography on silica gel to afford (1S,3R)-methyl 3-(thiazole-2-carbonyl)cyclopentanecarboxylate. MS ESI calc'd. for $C_{11}H_{14}NO_3S$ [M+H]$^+$ 240. found 240. $^1$H NMR (500 MHz, DMSO-d$_6$) δ 8.21 (d, J=3.0 Hz, 1H), 8.14 (d, J=3.0 Hz, 1H), 3.58 (s, 3H), 2.96-2.89 (m, 1H), 2.27-2.20 (m, 1H), 1.74-2.04 (m, 6H)

Intermediate 12. (1S,3R)-methyl 3-(1-hydroxy-1-(thiazol-2-yl)ethyl)cyclopentanecarboxylate

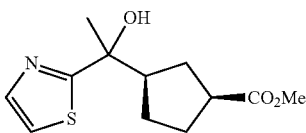 [SMILES: COC(=O)[C@H]1CC[C@@H](C(C)(O)c2nccs2)C1]

To a solution of (1S,3R)-methyl 3-(thiazole-2-carbonyl) cyclopentanecarboxylate (148 mg, 1.75 mmol) in THF (6 mL) and at −78° C. was added methylmagnesium bromide (582 mL, 1.75 mmol), the solution was stirred at −78° C. for 30 minutes. Saturated aqueous ammonium chloride was added and the mixture was allowed to warm to room temperature. The mixture was extracted with EtOAc, organic layer was dried over magnesium sulfate, filtered and concentrated in vacuo. The crude residue was absorbed on silica and purified by flash chromatography to afford (1S,3R)-methyl 3-(1-hydroxy-1-(thiazol-2-yl)ethyl)cyclopentanecarboxylate. MS ESI calc'd. for $C_{12}H_{18}NO_3S$ $[M+H]^+$ 256. found 256. $^1H$ NMR (500 MHz, DMSO-$d_6$) δ 7.67 (t, J=3.0 Hz, 1H), 7.50 (d, J=3.0 Hz, 1H), 3.58-3.57 (m, 3H), 3.52 (s, 1H), 2.75-2.62 (m, 1H), 2.43-2.35 (m, 1H), 1.97-1.91 (m, 1H), 1.78-1.51 (m, 4H), 1.46-1.44 (m, 3H), 1.25-1.19 (m, 1H).

Intermediate 13. Methyl (1S,4S)-4-[(1S)-1-hydroxy-1-(1,3-thiazol-2-yl)ethyl]-2,2-dimethylcyclohexanecarboxylate Methyl (1S,4S)-4-[(1R)-1-hydroxy-1-(1,3-thiazol-2-yl)ethyl]-2,2-dimethylcyclohexanecarboxylate
Methyl (1S,4R)-4-[(1S)-1-hydroxy-1-(1,3-thiazol-2-yl)ethyl]-2,2-dimethylcyclohexanecarboxylate
Methyl (1S,4R)-4-[(1R)-1-hydroxy-1-(1,3-thiazol-2-yl)ethyl]-2,2-dimethylcyclohexanecarboxylate

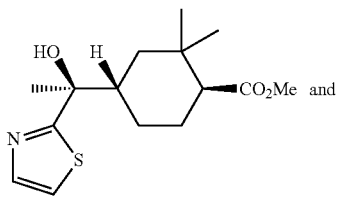
and

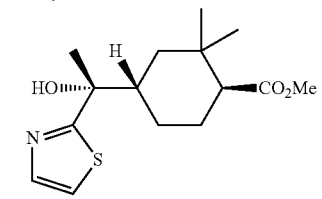

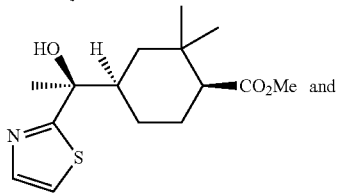
and

-continued

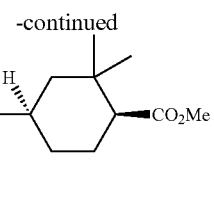

Step 1:
To a suspension of (methoxymethyl)triphenylphosphonium chloride (38 g, 111 mmol) in THF (300 mL) at 0° C. was added potassium tert-butoxide (1.0 M in THF, 111 mL, 111 mmol) at such a rate that the internal temperature did not exceed 7° C. After stirring for 1 hour at 0° C., a solution of methyl (1S)-2,2-dimethyl-4-oxocyclohexanecarboxylate (17 g, 92 mmol) in THF (100 mL) was added via canula at such a rate that the internal temperature did not exceed 7° C. Upon completion the mixture was slowly warmed to room temperature and stirred for 14 hours. The reaction mixture was then cooled to 10° C. and diluted with water (100 mL) followed by 6 M HCl (250 mL). The resulting mixture was stirred for 3 hours and then additional water (400 mL) and EtOAc (500 mL) were added. The organic layer was separated and the aqueous layer extracted a second time with EtOAc (500 mL). The combined organic layers were dried over $MgSO_4$, filtered, absorbed on silica gel, and purified by silica gel chromatography to afford a mixture of methyl (1R,4R)-4-formyl-2,2-dimethylcyclohexanecarboxylate and methyl (1R,4S)-4-formyl-2,2-dimethylcyclohexanecarboxylate. The product was used immediately in the subsequent step. To a cooled (−5° C.) solution of iPrMgCl—LiCl (1.3 M in THF, 64 mL, 83 mmol) was added thiazole (6.27 mL, 88 mmol) at such a rate that the internal temperature did not exceed 5° C. After the addition was complete, the resulting slurry was warmed to 15° C. over a period of 15 minutes, and then cooled to −10° C. To this slurry was added the mixture of (1R,4R)-4-formyl-2,2-dimethylcyclohexanecarboxylate and methyl (1R,4S)-4-formyl-2,2-dimethylcyclohexanecarboxylate (13.8 g, 69.6 mmol) as a solution in THF (30 mL) at such a rate the internal temperature did not exceed 5° C. The reaction mixture was stirred for 30 minutes at 0° C. and then quenched with water (50 mL). EtOAc (500 mL) and 1N HCl (300 mL) were added. The organic layer was separated, and the aqueous layer was extracted with EtOAc (500 mL). The organic layers were combined, dried over $MgSO_4$, filtered, absorbed on silica gel, and purified by silica gel chromatography to afford a diastereomeric mixture which was used immediately in the subsequent step.

To the above mixture of secondary alcohols (16.3 g, 575 mmol) in dichloromethane (150 mL) at 10° C. was added Dess-Martin periodinane (25.4 g, 60 mmol). Upon warming to room temperature, the temperature was controlled such that the internal temperature did not exceed 35° C. After 1 hour, the reaction mixture was cooled to room temperature and sequentially diluted with saturated aqueous $NaHCO_3$ solution (300 mL), aqueous 5% sodium sulfite solution (200 mL), and additional dichloromethane (350 mL). The heterogeneous mixture was stirred until both layers were clear, and then the layers were separated, and the aqueous layer was extracted a second time with dichloromethane (500 mL). The organic layers were combined, dried over $MgSO_4$, filtered, absorbed on silica, and purified by silica gel chromatography to afford a mixture of methyl (1S,4S)-2,2-dimethyl-4-(1,3-thiazol-2-ylcarbonyl)cyclohexanecarboxylate and methyl (1S,4R)-2,2-dimethyl-4-(1,3-thiazol-2-ylcarbonyl)cyclohexanecarboxylate. The mixture was further purified by SFC to afford the above compounds as single stereoisomers.

Characterization data for (1S,4S)-2,2-dimethyl-4-(1,3-thiazol-2-ylcarbonyl)cyclohexanecarboxylate: MS ESI calc'd. for $C_{14}H_{20}NO_3S$ [M+H]$^+$ 282. found 282. $^1$H NMR (600 MHz, CD$_3$OD) δ 8.04 (d, J 3.1 Hz, 1H), 7.93 (d, J=3.0 Hz, 1H), 3.85 (tt, J=12.5, 3.4 Hz, 1H), 3.64 (s, 3H), 2.24 (dd, J=12.8, 3.6 Hz, 1H), 2.00 (ddd, J=12.7, 5.6, 3.1 Hz, 1H), 1.88 (ddd, J=26.6, 13.6, 3.9 Hz, 1H), 1.75 (ddd, J=13.9, 7.0, 3.7 Hz, 1H), 1.69 (ddd, J=13.2, 3.1, 2.1 Hz, 1H), 1.46-1.35 (m, 2H), 1.05 (s, 3H), 1.01 (s, 3H).

Characterization data for (1S,4R)-2,2-dimethyl-4-(1,3-thiazol-2-ylcarbonyl)cyclohexanecarboxylate: MS ESI calc'd. for $C_{14}H_{20}NO_3S$ [M+H]$^+$ 282. found 282. $^1$H NMR (600 MHz, CD$_3$OD) δ 8.02 (d, J=3.1 Hz, 1H), 7.91 (d, J=3.1 Hz, 1H), 3.81 (tt, J=11.9, 3.8 Hz, 1H), 3.61 (s, 3H), 2.35 (d, J=3.8 Hz, 1H), 2.03 (t, J=12.6 Hz, 1H), 1.99-1.88 (m, 2H), 1.84-1.70 (m, 2H), 1.51-1.45 (m, 1H), 1.10 (s, 3H), 0.91 (s, 3H).

Step 2:

To a cooled (−40° C.) solution of (1S,4R)-2,2-dimethyl-4-(1,3-thiazol-2-ylcarbonyl)cyclohexanecarboxylate (2.3 g, 8.2 mmol) in THF (20 mL) was added MeMgBr (3.0 M in THF, 3.3 mL, 9.8 mmol) at such a rate that the internal temperature did not increase above −30° C. The mixture was then stirred for 15 minutes at −40° C., quenched with saturated aqueous ammonium chloride (40 mL), and warmed to room temperature. EtOAc (20 mL) was added, the layers were separated, and the aqueous layer was extracted a second time with EtOAc (30 mL). The organic layers were combined, dried over MgSO$_4$, filtered, absorbed on silica, and purified by silica gel chromatography to afford a mixture of methyl (1S,4R)-4-[(1S)-1-hydroxy-1-(1,3-thiazol-2-yl)ethyl]-2,2-dimethylcyclohexanecarboxylate and methyl (1S,4R)-4-[(1R)-1-hydroxy-1-(1,3-thiazol-2-yl)ethyl]-2,2-dimethylcyclohexanecarboxylate. Further purification was performed by SFC to afford the single diastereomers. MS ESI calc'd. for $C_{15}H_{24}NO_3S$ [M+H]$^+$ 298. found 298.

Step 3:

To a cooled (−40° C.) solution of (1S,4S)-2,2-dimethyl-4-(1,3-thiazol-2-ylcarbonyl)cyclohexanecarboxylate (11.6 g, 41.1 mmol) in THF (110 mL) was added MeMgBr (3.0 M in THF, 16.5 mL, 49.5 mmol) at such a rate the internal temperature did not increase above −30° C. The reaction mixture was stirred for 15 min at −40° C., quenched with saturated aqueous ammonium chloride (200 mL), and warmed to room temperature. EtOAc (110 mL) was added, the layers separated, and the aqueous layer was extracted a second time with EtOAc (110 mL). The organic layers were combined, dried over MgSO$_4$, filtered, absorbed on silica, and purified by silica gel chromatography to afford a mixture of methyl (1S,4S)-4-[(1S)-1-hydroxy-1-(1,3-thiazol-2-yl)ethyl]-2,2-dimethylcyclohexanecarboxylate and methyl (1S,4S)-4-[(1R)-1-hydroxy-1-(1,3-thiazol-2-yl)ethyl]-2,2-dimethylcyclohexanecarboxylate. Further purification was performed by SFC to afford the single diastereomers.

Characterization data for Peak 1 from SFC: MS ESI calc'd. for $C_{15}H_{24}NO_3S$ [M+H]$^+$ 298. found 298. $^1$H NMR (500 MHz, DMSO-d$_6$) δ 7.68 (d, J=3.3 Hz, 1H), 7.50 (d, J=3.2 Hz, 1H), 5.71 (s, 1H), 3.53 (s, 3H), 1.98 (dd, J=3.9, 12.5 Hz, 1H), 1.89 (tt, J=3.3, 12.3 Hz, 1H), 1.83-1.75 (m, 1H), 1.65-1.49 (m, 2H), 1.42 (s, 3H), 1.14 (t, J=12.7 Hz, 114), 1.08-1.01 (m, 1H), 0.98-0.88 (m, 1H), 0.84 (s, 3H), 0.77 (s, 3H).

Characterization data for Peak 2 from SFC: MS ESI calc'd. for $C_{15}H_{24}NO_3S$ [M+H]$^+$ 298. found 298. $^1$H NMR (500 MHz, DMSO-d$_6$) δ 7.68 (d, J=3.3 Hz, 1H), 7.51 (d, J=3.3 Hz, 1H), 5.71 (s, 1H), 3.53 (s, 3H), 1.98 (dd, J=3.9, 12.4 Hz, 1H), 1.86 (tt, J=3.2, 12.5 Hz, 1H), 1.58-1.51 (m, 1H), 1.51 (s, 2H), 1.43 (s, 3H), 1.41-1.33 (m, 1H), 1.16-1.06 (m, 1H), 0.93 (t, J=12.3 Hz, 1H), 0.90 (s, 314), 0.83 (s, 3H).

Intermediate 14. Ethyl 4-[1-hydroxy-1-(1,3-thiazol-2-yl)ethyl]-2-methylcyclohexanecarboxylate

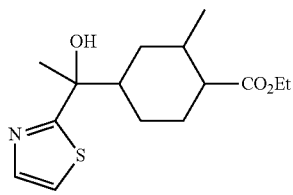 [SMILES: CCOC(=O)C1CCC(C(C)(O)c2nccs2)CC1C]

Step 1:

To a cooled (0° C.) suspension of (methoxymethyl)triphenylphosphonium chloride (155 g, 452 mmol) in THF (700 mL) was added potassium tert-butoxide (1.0 M in THF, 452 mL, 452 mmol) at such a rate that the internal temperature did not exceed 7° C. The mixture was stirred for 1 hour at 0° C., and then a solution of ethyl 2-methyl-4-oxocyclohexanecarboxylate (64 g, 347 mmol) in THF (150 mL) was added via canula at such a rate that the internal temperature did not exceed 7° C. The mixture was then slowly warmed to room temperature and stirred for 14 hours. The reaction mixture was then cooled to 10° C. and diluted with water (200 mL) followed by 6 M HCl (500 mL). The resulting mixture was stirred for 3 hours, and then diluted with additional water (400 mL) and EtOAc (700 mL). The organic layer was separated, and the aqueous layer was extracted a second time with EtOAc (700 mL). The organic layers were combined, dried over MgSO$_4$, filtered, absorbed on silica gel, and purified by silica gel chromatography to afford ethyl 4-formyl-2-methylcyclohexanecarboxylate, which was used immediately in the subsequent step.

To a cooled solution of iPrMgCl—LiCl (1.3 M in THF, 187 mL, 243 mmol) at −5° C. was added thiazole (17.4 mL, 243 mmol) at such a rate that the internal temperature did not exceed 5° C. The resulting slurry was warmed to 15° C. over 15 minutes, and then cooled to −10° C. To the reaction mixture was added ethyl 4-formyl-2-methylcyclohexanecarboxylate (41 g, 207 mmol) as a solution in THF (100 mL) at such a rate the internal temperature did not exceed 5° C. The reaction mixture was stirred for 30 minutes at 0° C., and then quenched with water (100 mL) and diluted with EtOAc (500 mL) and 1N HCl (500 mL). The organic layer was separated, and the aqueous layer extracted again with EtOAc (700 mL). The organic layers were combined, dried over MgSO$_4$, filtered, and concentrated under reduced pressure. The residue was diluted with DCM (500 mL), and to this mixture was added Dess-Martin periodinane (88 g, 208 mmol). During the addition, the temperature was controlled such that the internal temperature did not exceed 35° C. After 1 hour, the reaction mixture was cooled to room temperature and then diluted with saturated aqueous NaHCO$_3$ (600 mL), aqueous 5% sodium sulfite (600 mL), and dichloromethane (600 mL). The heterogeneous mixture was stirred until both layers were clear. The layers were separated and the aqueous layer was extracted a second time with dichloromethane (600 mL). The organic layers were combined, dried over MgSO$_4$, filtered, absorbed on silica, and purified by silica gel chromatography to afford ethyl 2-methyl-4-(1,3-thiazol-2-ylcarbonyl)cyclohexanecarboxylate. MS ESI calc'd. for $C_{14}H_{20}NO_3S$ [M+H]$^+$ 282. found 282.

Step 2:

To a solution of ethyl 2-methyl-4-(1,3-thiazol-2-ylcarbonyl)cyclohexanecarboxylate (2.8 g, 10 mmol) in THF (28 mL) at −40° C. was added MeMgBr (3.0 M in THF, 4.0 mL, 12 mmol) at such a rate the internal temperature did not exceed −30° C. The reaction mixture was stirred for 15 minutes at −40° C., and was then quenched with saturated aqueous ammonium chloride (50 mL) and warmed to room temperature. EtOAc (20 mL) was added, the layers separated, and the aqueous layer was extracted a second time with EtOAc (50 mL). The organic layers were combined, dried over MgSO$_4$, filtered, absorbed on silica, and purified by silica gel chromatography to afford ethyl 4-[1-hydroxy-1-(1,3-thiazol-2-yl)ethyl]-2-methylcyclohexanecarboxylate.

The mixture of stereoisomers were separated into 4 fractions in order of increasing elution time by SFC (ES Industries GreenSep Pyridyl Amide, 21×250 mm, 5 micron, 5% MeOH/95% CO$_2$, 50 mL/min). These 4 fractions were then separated further using the following conditions (Chiralpak AD-H 21×250 mm, 5 micron, 220 nm UV, 100 bar outlet pressure, 70 mL/min). The respective solvents used are shown in FIG. 1

Intermediate 15: (4R)-4-[(1S)-1-hydroxy-1-(1,3-thiazol-2-yl)ethyl]pyrrolidin-2-one (4R)-4-[(1R)-1-hydroxy-1-(1,3-thiazol-2-yl)ethyl]pyrrolidin-2-one

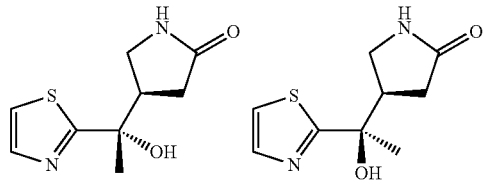

Step 1:

To a solution of thiazole (3.13 mL, 44 mmol) in THF (50 mL) at −78° C. was added nBuLi at such a rate that the internal temperature did not exceed −65° C. The reaction mixture was stirred for 15 minutes, and then a solution of (4R)-4-acetyl-1-[(1S)-1-(4-methoxyphenyl)ethyl]pyrrolidin-2-one (10 g, 38.3 mmol) in THF (50 mL) was added via canula at such a rate that the internal temperature did not exceed −65° C. The mixture was stirred for 1 hour, quenched with saturated aqueous ammonium chloride (50 mL), and warmed to room temperature. EtOAc (50 mL) and water (50 mL) were added. The layers were separated, and the aqueous layer was extracted a second time with EtOAc (50 mL). The organic layers were combined, dried over MgSO$_4$, filtered, absorbed on silica, and purified by silica gel chromatography to afford (4R)-4-[(1S)-1-hydroxy-1-(1,3-thiazol-2-yl)ethyl]-1-[(1S)-1-(4-methoxyphenyl)ethyl]pyrrolidin-2-one and (4R)-4-[(1R)-1-hydroxy-1-(1,3-thiazol-2-yl)ethyl]-1-[(1S)-1-(4-methoxyphenyl)ethyl]pyrrolidin-2-one.

Characterization data for the less polar diastereomer, (4R)-4-[(1S)-1-hydroxy-1-(1,3-thiazol-2-yl)ethyl]-1-[(1S)-1-(4-methoxyphenyl)ethyl]pyrrolidin-2-one: MS ESI calc'd. for $C_{18}H_{23}N_2O_3S$ [M+H]$^+$ 347. found 347. $^1$H NMR (600 MHz, DMSO-d$_6$) δ 7.67 (d, J=3.2 Hz, 1H), 7.51 (d, =3.2 Hz, 1H), 7.00 (d, J=8.5 Hz, 2H), 6.81 (d, J=8.7 Hz, 2H), 6.08 (s, 1H), 5.10 (q, J=7.1 Hz, 1H), 3.70 (s, 3H), 3.35 (t, J=9.4 Hz, 1H), 2.89 (dd, J=9.8, 7.1 Hz, 1H), 2.82-2.72 (m, 1H), 2.43 (dd, J=16.9, 8.2 Hz, 1H), 2.00 (dd, J=16.9, 9.8 Hz, 1H), 1.37-1.35 (m, 6H).

Characterization data for the more polar diastereomer, (4R)-4-[(1R)-1-hydroxy-1-(1,3-thiazol-2-yl)ethyl]-1-[(1S)-1-(4-methoxyphenyl)ethyl]pyrrolidin-2-one: MS ESI calc'd. for $C_{18}H_{23}N_2O_3S$ [M+H]$^+$ 347. found 347. $^1$H NMR (600 MHz, DMSO-d$_6$) δ 7.66 (d, J=3.2 Hz, 1H), 7.51 (d, J=3.2 Hz, 1H), 7.08 (d, J=8.5 Hz, 2H), 6.83 (d, J=8.4 Hz, 2H), 6.08 (s, 1H), 5.14 (dd, J=14.2, 7.0 Hz, 1H), 3.70 (s, 3H), 2.99-2.90 (m, 1H), 2.88-2.78 (m, 2H), 2.40-2.30 (m, 2H), 1.33 (s, 3H), 1.30 (d, J=7.1 Hz, 3H).

Step 2:

A solution of (4R)-4-[(1S)-1-hydroxy-1-(1,3-thiazol-2-yl)ethyl]-1-[(1S)-1-(4-methoxyphenyl)ethyl]pyrrolidin-2-one (3.6 g, 10.4 mmol) in TFA (10 mL) was heated to 70° C. for 5 hours. The reaction mixture was cooled to room temperature, diluted with IPA (30 mL), and stirred until the color dissipated. The reaction mixture was then absorbed on silica gel and purified by silica gel chromatography to afford (4R)-4-[(1S)-1-hydroxy-1-(1,3-thiazol-2-yl)ethyl]pyrrolidin-2-one. MS ESI calc'd. for $C_9H_{13}N_2O_2S$ [M+H]$^+$ 213. found 213. $^1$H NMR (600 MHz, DMSO-d$_6$) δ 7.68 (d, J=3.2 Hz, 1H), 7.54 (d, J=3.2 Hz, 1H), 7.39 (s, 1H), 6.10 (s, 1H), 3.25 (t, J=9.2 Hz, 1H), 3.19 (dd, J=9.6, 7.4 Hz, 1H), 2.91-2.81 (m, 1H), 2.20 (dd, J=16.7, 8.6 Hz, 1H), 1.77 (dd, J=16.7, 9.6 Hz, 1H), 1.43 (s, 3H).

Step 3:

A solution of (4R)-4-[(1R)-1-hydroxy-1-(1,3-thiazol-2-yl)ethyl]-1-[(1S)-1-(4-methoxyphenyl)ethyl]pyrrolidin-2-one (3.6 g, 10.4 mmol) in TFA (10 mL) was heated to 70° C. for 5 hours. The reaction mixture was cooled to room temperature, diluted with IPA (30 mL), and stirred until the color dissipated. The reaction mixture was then absorbed on silica gel and purified by silica gel chromatography to afford (4R)-4-[(1R)-1-hydroxy-1-(1,3-thiazol-2-yl)ethyl]pyrrolidin-2-one. MS ESI calc'd. for $C_9H_{13}N_2O_2S$ [M+H]$^+$ 213. found 213. $^1$H NMR (600 MHz, DMSO-d$_6$) δ 7.69 (d, J=3.2 Hz, 1H), 7.54 (d, J=3.2 Hz, 1H), 7.35 (s, 1H), 6.12 (s, 1H), 3.08

(dd, J=9.1, 7.3 Hz, 1H), 2.96-2.86 (m, 1H), 2.82 (t, J=9.0 Hz, 1H), 2.22 (dd, J=16.8, 8.7 Hz, 1H), 2.14 (dd, J=16.8, 9.6 Hz, 1H), 1.42 (s, 3H).

Example 1 racemic trans-4-[1-(5-{6-[(4-Cyclopropylpyridin-2-yl)amino]-4-methylpyridin-2-yl}-1,3-thiazol-2-yl)-1-hydroxypropyl]cyclohexanecarboxylic acid, trans-4-[(1R)-1-(5-{6-[(4-cyclopropylpyridin-2-yl)amino]-4-methylpyridin-2-yl}-1,3-thiazol-2-yl)-1-hydroxypropyl]cyclohexanecarboxylic acid, and trans-4-[(1S)-1-(5-{6-[(4-cyclopropylpyridin-2-yl)amino]-4-methylpyridin-2-yl}-1,3-thiazol-2-yl)-1-hydroxypropyl]cyclohexanecarboxylic acid

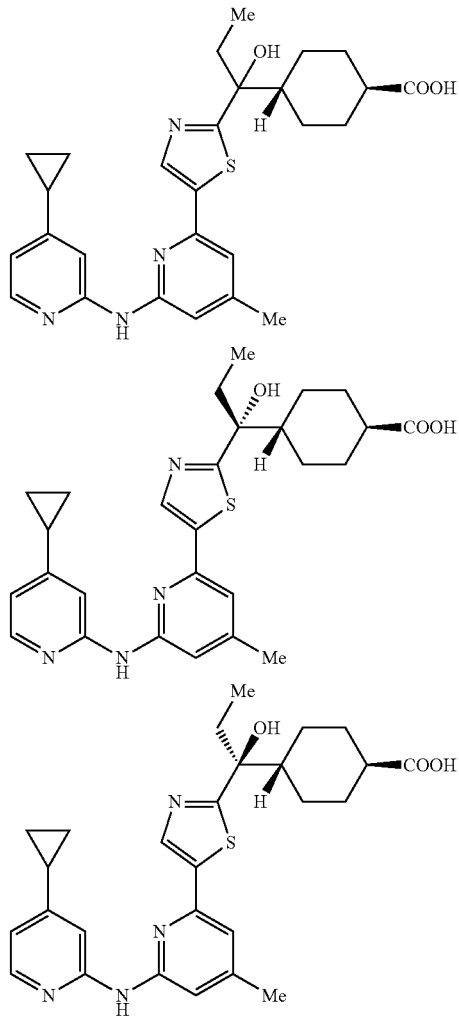

Step 1:

A dry round bottom flask was charged with trans-4-(methoxycarbonyl)cyclohexanecarboxylic acid (2.00 g, 10.74 mmol) and the reaction vessel was placed under an atmosphere of argon (3× vacuum/argon cycle). Dichloromethane (11 mL) was added followed by DMF (0.01 mL, 0.129 mmol). The reaction was cooled to 0° C. in an ice bath, then oxalyl chloride (1.00 mL, 11.42 mmoles) was added drop-wise. The ice bath was removed after 1 hour and the reaction was stirred at ambient temperature for 14 hours as gradual gas evolution occurred. [1,1'-Bis(diphenylphosphino)ferrocene]-dichloropalladium(II) (236.0 mg, 0.322 mmol) was then added to the reaction flask followed by tetrahydrofuran (11 mL) then a solution of diethylzinc in tetrahydrofuran (1.0 M, 12.9 mL, 12.9 mmol). The reaction was stirred at ambient temperature for two hours and was then poured into cold saturated aqueous ammonium chloride (100 mL). The resulting biphasic solution was diluted with diethyl ether (100 mL). The organic phase was separated and dried over magnesium sulfate, filtered, and concentrated under reduced pressure. The residue was purified by silica gel chromatography (0-100% ethyl acetate/hexanes) to afford methyl trans-4-propanoylcyclohexanecarboxylate as a clear oil. $^1$H NMR (500 MHz, CDCl$_3$) δ 3.67 (s, 3H), 2.47 (q, J=7.3 Hz, 2H), 2.40-2.21 (m, 2H), 2.12-2.00 (m, 2H), 1.94 (d, J=13.9 Hz, 2H), 1.53-1.20 (m, 4H), 1.03 (t, J=7.3 Hz, 3H).

Step 2:

Isopropyl magnesium chloride lithium chloride (1.3 M in THF, 6.66 mL, 8.66 mmol) was added drop-wise to a solution of thiazole (0.675 mL, 9.44 mmol) in THF (5 mL) at 0° C. The reaction was stirred for 30 minutes and the ice bath was removed. Stirring was then continued for 10 minutes before the reaction was re-cooled in an acetone/dry ice bath, then a solution of methyl trans-4-propanoylcyclohexanecarboxylate (1.56 g, 7.87 mmol) in THF (15 mL) was transferred in via cannula. The reaction was stirred for 1 hour and the cooling bath was removed. Once warming was complete (~1 hour) the reaction was diluted with saturated aqueous ammonium chloride (75 mL) and the resulting biphasic mixture was transferred to a separatory funnel. The organic phase was diluted with ethyl acetate (125 mL). The organic phase was separated, dried over magnesium sulfate, filtered and concentrated under reduced pressure. The residue was purified by silica gel chromatography (0-100% ethyl acetate/hexanes) to afford trans-methyl 4-[1-hydroxy-1-(1,3-thiazol-2-yl)propyl]cyclohexanecarboxylate. MS ESI calc'd. for $C_{14}H_{22}NO_3S$ [M+H]$^+$ 284. found 284. $^1$H NMR (500 MHz, DMSO-d$_6$) δ 7.70 (d, J=3.3 Hz, 1H), 7.49 (d, J=3.3 Hz, 1H), 3.53 (s, 3H), 2.07 (t, J=12.1 Hz, 1H), 1.95-1.63 (m, 4H), 1.44-1.06 (m, 6H), 1.01-0.81 (m, 2H), 0.65 (t, J=7.3 Hz, 3H).

Step 3:

6-Bromo-N-(4-cyclopropylpyridin-2-yl)-4-methylpyridin-2-amine (263 mg, 0.865 mmol), trans-methyl 4-[1-hydroxy-1-(1,3-thiazol-2-yl)propyl]cyclohexanecarboxylate (245 mg, 0.865 mmol), pivalic acid (151 μl, 1.297 mmol), potassium carbonate (358 mg, 2.59 mmol), π-allyl palladium (II)chloride dimer (31.6 mg, 0.086 mmol) and butyl di-1-adamantylphosphine (124 mg, 0.346 mmol) were combined and the reaction flask was put under inert atmosphere (3× vacuum/argon cycle) then degassed dimethylacetamide (2 mL) was added. The reaction was heated to 100° C. for 5 hours, then cooled to room temperature and poured into diethyl ether (100 mL). The resulting solution was transferred to a separatory funnel and sequentially washed with water (3×50 mL) and sodium bicarbonate (50 mL), dried over magnesium sulfate, filtered and concentrated under reduced pressure. The resulting crude oil was purified by silica gel chromatography (0-100% ethyl acetate/hexanes) to afford methyl trans-4-[1-(5-{6-[(4-cyclopropylpyridin-2-yl)amino]-4-methylpyridin-2-yl}-1,3-thiazol-2-yl)-1-hydroxypropyl]cyclohexanecarboxylate as a yellow foam. MS ESI calc'd. for $C_{28}H_{35}N_4O_3S$ [M+H]$^+$ 507. found 507. $^1$H NMR (500 MHz, CDCl$_3$) δ 8.12-8.04 (m, 2H), 7.71 (s, 1H), 7.23 (s, 1H), 7.05 (s, 1H), 6.86 (s, 1H), 6.66 (d, J=5.2 Hz, 1H), 3.64 (s, 3H), 2.35 (s, 3H), 2.28-2.16 (m, 1H), 2.16-1.86 (m, 8H), 1.51-1.30 (m, 3H), 1.26 (t, J=7.1 Hz, 1H), 1.21-1.06 (m, 3H), 1.03-0.93 (m, 2H), 0.83 (t, J=7.2 Hz, 3H).

Step 4:

To a flask containing methyl trans-4-[1-(5-{6-[(4-cyclopropylpyridin-2-yl)amino]-4-methylpyridin-2-yl}-1,3-thiazol-2-yl)-1-hydroxypropyl]-cyclohexanecarboxylate (198 mg, 0.391 mmol) and potassium hydroxide (88 mg, 1.563 mmol) was added methanol (1 mL) and water (1 mL). The reaction vessel was sealed and heated to 80° C. for a period of 14 hours. After cooling the reaction, aqueous hydrochloric acid (1.0 M, 1.56 mL, 1.56 mmol) was added. The cloudy solution was diluted with additional water (10 mL) and stirring was continued for one hour. Chloroform and isopropanol (4:1; 20 mL total) were added and the biphasic mixture was transferred to a separatory funnel. The organic phase was separated, dried over sodium sulfate, filtered and concentrated under reduced pressure to yield trans-4-[1-(5-{6-[(4-cyclopropylpyridin-2-yl)amino]-4-methylpyridin-2-yl}-1,3-thiazol-2-yl)-1-hydroxypropyl]cyclohexanecarboxylic acid. MS ESI calc'd. for $C_{27}H_{33}N_4O_3S$ [M+H]$^+$ 493. found 493. $^1$H NMR (500 MHz, DMSO-d$_6$) δ 11.60-10.74 (br s, 1H), 8.48 (s, 1H), 8.27 (s, 1H), 7.75-7.29 (m, 2H), 7.26 (m, 2H), 5.68-5.47 (m, 1H), 2.42 (s, 3H), 2.29-2.12 (m, 1H), 2.12-1.84 (m, 7H), 1.84-1.73 (m, 1H), 1.54-1.42 (m, 1H), 1.43-1.13 (m, 6H), 1.13-0.97 (m, 3H), 0.88 (t, J=7.3 Hz, 3H). rhSyk activity=+++.

Two enantiomers were separated by chiral super critical fluid chromatography (Chiral Technology AS-H, 2.1×25 cm, 5 uM, 3/1 MeOH/CO$_2$+0.25% TFA, Flow Rate: 70 mL/min, 10 min run time, WL: 220 nm). Elution was observed at 7.03 min and 8.08 min. Pooled fractions of each peak were concentrated under reduced pressure.

Enantiomer 1 (retention time=7.03 min): MS ESI calc'd. for $C_{27}H_{33}N_4O_3S$ [M+H]$^+$ 493. found 493. $^1$H NMR (500 MHz, DMSO-d$_6$) spectrum was consistent with the $^1$H NMR spectrum of the racemic material. rhSyk activity=+++.

Enantiomer 2 (retention time=8.08 min): MS ESI calc'd. for $C_{27}H_{33}N_4O_3S$ [M+H]$^+$ 493. found 493. $^1$H NMR (500 MHz, DMSO-d$_6$) spectrum was consistent with the $^1$H NMR spectrum of the racemic material. rhSyk activity=+++.

Example 2 trans-4-[1-(5-{6-[(4-cyclopropylpyridin-2-yl)amino]-4-methylpyridin-2-yl}-1,3-thiazol-2-yl)-1-hydroxypropyl]cyclohexanecarboxamide, trans-4-[(1R)-1-(5-{6-[(4-cyclopropylpyridin-2-yl)amino]-4-methylpyridin-2-yl}-1,3-thiazol-2-yl)-1-hydroxypropyl]cyclohexanecarboxamide, trans-4-[(1S)-1-(5-{6-[(4-cyclopropylpyridin-2-yl)amino]-4-methylpyridin-2-yl}-1,3-thiazol-2-yl)-1-hydroxypropyl]cyclohexanecarboxamide

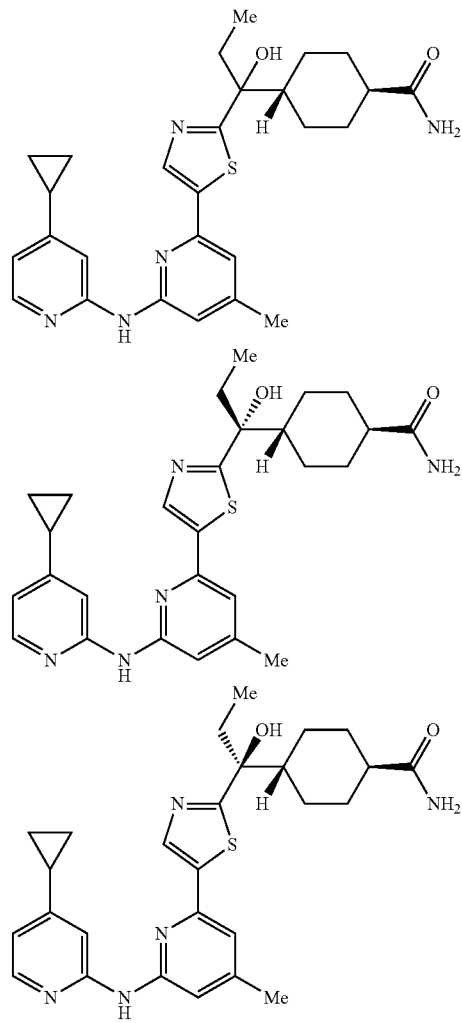

To a flask containing racemic trans-4-[1-(5-{6-[(4-cyclopropylpyridin-2-yl)amino]-4-methylpyridin-2-yl}-1,3-thiazol-2-yl)-1-hydroxypropyl]cyclohexanecarboxylic acid (25 mg, 0.051 mmol) was added O-(7-azabenzotriazol-1-yl)-N,N,N',N'-tetramethyluronium hexafluorophosphate (25.1 mg, 0.066 mmol) and ammonium chloride (10.9 mg, 0.203 mmol). DMF (1 mL) and N,N-diisopropylethylamine (0.089 mL, 0.507 mmol) were added and the reaction was sealed and stirred for 2 hours. Methanol (0.1 mL) was then added to quench the reaction and the resulting solution was filtered.

The filtrate was purified by reversed phase HPLC (10-100% acetonitrile/water with 0.1% TFA). The fractions containing desired product were pooled, frozen and concentrated to dryness on a lyophilizer to afford trans-4-[1-(5-{6-[(4-cyclopropylpyridin-2-yl)amino]-4-methylpyridin-2-yl}-1,3-thiazol-2-yl)-1-hydroxypropyl]cyclohexanecarboxamide. MS ESI calc'd. for $C_{27}H_{34}N_5O_2S$ [M+H]$^+$ 492. found 492. $^1$H NMR (500 MHz, DMSO-d$_6$) δ 11.31 (s, 1H), 8.49 (s, 1H), 8.30 (d, J=6.4 Hz, 1H), 7.53 (s, 1H), 7.38 (s, 1H), 7.15 (s, 1H), 7.04 (d, J=6.4 Hz, 1H), 6.94 (s, 1H), 6.68 (s, 1H), 5.84-5.30 (m, 1H), 2.43 (s, 3H), 2.30-2.15 (m, 1H), 2.07-1.87 (m, 4H), 1.87-1.67 (m, 3H), 1.54-1.42 (m, 1H), 1.42-1.18 (m, 6H), 1.12-0.93 (m, 3H), 0.79 (t, J=7.3 Hz, 3H) ppm. rhSyk=+++.

The procedure above was used on the enantiopure acids obtained from chiral SFC resolution of the racemic starting material above (Example 1, Step 4).

Starting with (Example 1, Step 4, Enantiomer 1, R$_t$=7.03 min): MS ESI calc'd. for $C_{27}H_{34}N_5O_2S$ [M+H]$^+$ 492. found 492. $^1$H NMR (500 MHz, DMSO-d$_6$) spectrum was consistent with the $^1$H NMR spectrum of the racemic material. rhSyk activity=+++. Starting with (Example 1, Step 4, Enantiomer 2, R$_t$=8.08 min): MS ESI calc'd. for $C_{27}H_{34}N_5O_2S$ [M+H]$^+$ 492. found 492. $^1$H NMR (500 MHz, DMSO-d$_6$) spectrum was consistent with the $^1$H NMR spectrum of the racemic material. rhSyk activity=+++.

Example 3 trans-4-{(1R or 1S)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid (Enantiomer 2)

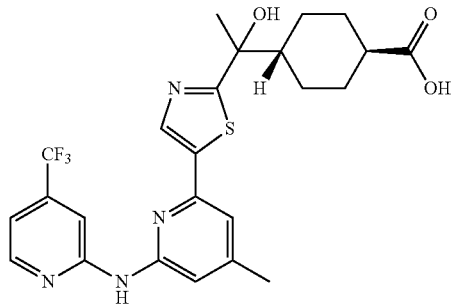 [SMILES: Cc1cc(Nc2cc(C(F)(F)F)ccn2)nc(-c2cnc(C(C)(O)[C@H]3CC[C@H](C(=O)O)CC3)s2)c1]

Step 1:

To a flask were added cis-cyclohexane-1,4-dicarboxylic acid (20 g, 116 mmol), n-butyl formate (581 ml, 5066 mmol), Dowex 50W×2 resin (87 grams), and octane (484 ml). The reaction mixture was heated to 110° C. overnight and then cooled and filtered. The resin was washed with 300 mL 1:1 hexane:EtOAc. The filtrate was concentrated and then taken up in toluene and re-concentrated. The resulting residue was dissolved in dichloromethane (119 ml) and then thionyl chloride (11.51 ml, 158 mmol) was added. The reaction mixture was heated to 38° C. overnight and then concentrated. The residue was taken up in DCM and re-concentrated (3×) to remove residual HCl. The resulting residue was dissolved in 1,4-dioxane (413 ml) and degassed with Ar for 30 minutes. Palladium (II) acetate (0.696 g, 3.10 mmol) was added and the mixture was degassed for an additional 30 minutes. Dimethyl zinc (2 M in toluene, 31.0 ml, 62.0 mmol) was added. The system was placed under argon through 3 cycles of evacuation and argon flushing then reacted at 38° C. overnight. The reaction mixture was cooled and diluted with water. The resulting mixture was filtered through a CELITE plug and then the solid was washed with EtOAc. The filtrate was concentrated and purified by column chromatography on silica gel (0-30% ethyl acetate/hexanes) to afford butyl cis-4-acetylcyclohexanecarboxylate. $^1$H NMR (500 MHz, DMSO-d$_6$) δ 4.07 (t, J=6.6 Hz, 2H), 2.54-2.48 (m, 1H), 2.44-2.38 (m, 1H), 2.13 (s, 3H), 2.01-1.93 (m, 2H), 1.81-1.57 (m, 9H), 1.41-1.32 (m, 2H), 0.92 (t, J=7.5 Hz, 3H).

Step 2:

A solution of thiazole (800 mg, 9.40 mmol) in THF (94 mL) was cooled to −78° C. nBuLi (2.5 M in THF, 3759 μl, 9.40 mmol) was added and the solution was stirred for 30 minutes at −78° C. Butyl cis-4-acetylcyclohexanecarboxylate (2552 mg, 11.28 mmol) in THF (5 mL) was added in one portion and the solution was stirred for one hour at −78° C. The reaction was diluted with water and then warmed to room temperature. The mixture was extracted with ethyl acetate and the organic layer was dried over magnesium sulfate, filtered and concentrated under reduced pressure. The residue was purified by column chromatography on silica gel (5-30% ethyl acetate/hexanes) to afford cis-butyl 4-[1-hydroxy-1-(1,3-thiazol-2-yl)ethyl]cyclohexanecarboxylate. MS ESI calc'd. for $C_{16}H_{25}NO_3S$ [M+H]$^+$ 312. found 312.

Step 3:

To a vial were added 2,6-dibromo-4-methylpyridine (121 mg, 0.482 mmol), cis-butyl 4-[1-hydroxy-1-(1,3-thiazol-2-yl)ethyl]cyclohexanecarboxylate (75 mg, 0.241 mmol), potassium carbonate (100 mg, 0.722 mmol), pivalic acid (5.59 μl, 0.048 mmol), tetrakis(triphenylphosphine)palladium(0) (11.1 mg, 9.63 μmol) and N,N-dimethylacetamide (760 μl). The vial was sealed and placed under argon through 3 cycles of evacuation and argon flushing then reacted at 80° C. overnight. The resulting mixture was cooled, diluted with ethyl acetate, filtered through a plug of CELITE and concentrated. The residue was purified by column chromatography on silica gel (0-100% ethyl acetate/hexanes) to afford racemic-cis-butyl 4-{1-[5-(6-bromo-4-methylpyridin-2-yl)-1,3-thiazol-2-yl]-1-hydroxyethyl}-cyclohexanecarboxylate.

Two enantiomers were separated by chiral super critical fluid chromatography (Chiral Technology IC-H, 2.1×25 cm, 5 uM, 70/30 ethanol/CO$_2$, Flow Rate: 70 mL/min, 8 min run time, WL: 220 nm). Elution was observed at 5.20 min and 6.08 min. Pooled fractions of each peak were concentrated under reduced pressure.

Enantiomer 1 (retention time 5.20 min): MS ESI calc'd. for $C_{22}H_{29}BrF_3N_2O_3S$ [M+H]$^+$ 481 and 483. found 481 and 483.

Enantiomer 2 (retention time 6.08 min): MS ESI calc'd. for $C_{22}H_{29}BrF_3N_2O_3S$ [M+H]$^+$ 481 and 483. found 481 and 483.

Step 4:

To a vial were added 4-(trifluoromethyl)pyridin-2-amine (10 mg, 0.062 mmol), cis-butyl 4-{1-[5-(6-bromo-4-methylpyridin-2-yl)-1,3-thiazol-2-yl]-1-hydroxyethyl}-cyclohexanecarboxylate (Step 3, Enantiomer 1, R$_t$=5.20 min) (14.9 mg, 0.031 mmol), palladium(II) acetate (0.7 mg, 3 μmol), Xantphos (2.7 mg, 4.6 μmol), cesium carbonate (20.1 mg, 0.062 mmol) and 1,4-dioxane (308 μl). The vial was sealed and placed under argon through 3 cycles of evacuation and argon flushing followed by heating at 100° C. for 2 hr and 30 minutes. The mixture was cooled, diluted with EtOAc, filtered through a plug of CELITE and concentrated under reduced pressure. The residue was purified by column chromatography on silica gel (0-100% ethyl acetate/hexanes) to afford butyl 4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylate. MS ESI calc'd. for $C_{28}H_{33}F_3N_4O_3S$ [M+H]$^+$ 563. found 563.

Step 5:
To a vial were added butyl 4-{(1R or 1S)-1-[5-(6-bromo-4-methylpyridin-2-yl)-1,3-thiazol-2-yl]-1-hydroxyethyl}cyclohexanecarboxylate (10 mg, 0.018 mmol), MeOH (178 μl) and NaOH (1 M in water, 89 μl, 0.089 mmol). The vial was sealed and heated in a microwave for 10 minutes at 100° C. An additional 25 uL NaOH was added and then heated in a microwave for 20 minutes. Then, the pH was adjusted to 3-4 with 1 M aqueous HCl. The solution was diluted with 10% IPA/CHCl$_3$ and washed with water and brine. The organic layer was separated by passing through a hydrophobic membrane cartridge and concentrated to afford trans-4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid. MS ESI calc'd. for $C_{24}H_{25}F_3N_4O_3S$ [M+H$^+$] 507. found 507. $^1$H NMR (500 MHz, DMSO-d$_6$) δ 10.19 (s, 1H), 8.64 (s, 1H), 8.48 (d, J=5.0 Hz, 1H), 8.26 (s, 1H), 7.34 (s, 1H), 7.21 (d, J=5.0 Hz, 1H), 7.08 (s, 1H), 2.31 (s, 3H), 2.06-1.67 (m, 3H), 1.67-1.34 (m, 5H), 1.31-0.96 (m, 5H). rhSyk activity=+++.

Example 4 trans-4-{(1R or 1S)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid (Enantiomer 1)

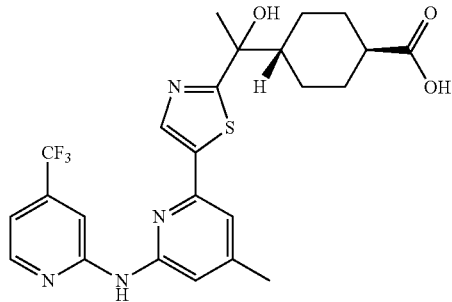 [SMILES: Cc1cc(Nc2cc(C(F)(F)F)ccn2)nc(-c2cnc(C(C)(O)[C@H]3CC[C@H](C(=O)O)CC3)s2)c1]

Step 1:
To a vial were added 4-(trifluoromethyl)pyridin-2-amine (8 mg, 0.049 mmol), cis-butyl 4-{1-[5-(6-bromo-4-methylpyridin-2-yl)-1,3-thiazol-2-yl]-1-hydroxyethyl}-cyclohexanecarboxylate (Example 3, Step 3, Enantiomer 2, R$_t$=6.08 min) (11.9 mg, 0.025 mmol), palladium(II) acetate (0.6 mg, 2.47 μmol), Xantphos (2.1 mg, 3.7 μmol), cesium carbonate (16.1 mg, 0.049 mmol) and 1,4-dioxane (2470). The vial was sealed and placed under argon through 3 cycles of evacuation and argon flushing then reacted at 100° C. overnight. The resulting mixture was cooled, diluted with EtOAc, filtered through a plug of CELITE and concentrated. The residue was purified by column chromatography on silica (0-100% ethyl acetate/hexanes) to afford butyl 4-{(1R or 1S)-1-hydroxy-1-[5-(4-methyl-6-{[4-(trifluoromethyl)pyridin-2-yl]amino}-pyridin-2-yl)-1,3-thiazol-2-yl]ethyl}cyclohexanecarboxylate. MS ESI calc'd. for $C_{28}H_{33}F_3N_4O_3S$ [M+H$^+$] 563. found 563.

Step 2:
To a vial were added butyl 4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}-cyclohexanecarboxylate (10 mg, 0.018 mmol), MeOH (178 μl) and NaOH (1 M in water, 89 μl, 0.089 mmol). The vial was sealed and placed under argon through 3 cycles of evacuation and argon flushing and then heated in a microwave for 10 minutes at 100° C. Then, the pH was adjusted pH to 3-4 with 1M HCl. The solution was diluted with 10% IPA/CHCl$_3$ and washed with water and brine. The organic layer was separated by passing through a hydrophobic membrane cartridge and concentrated to afford trans-4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid. MS ESI calc'd. for $C_{24}H_{25}F_3N_4O_3S$ [M+H+] 507. found 507. $^1$H NMR (500 MHz, DMSO-d$_6$) δ 10.18 (s, 1H), 8.64 (s, 1H), 8.48 (d, J=5.3 Hz, 1H), 8.26 (s, 1H), 7.34 (s, 1H), 7.20 (d, J=5.5 Hz, 1H), 7.08 (s, 1H), 2.31 (s, 3H), 2.15-1.72 (m, 3H), 1.72-1.32 (m, 5H), 1.31-0.87 (m, 5H). rhSyk activity=+++.

Example 5 trans-4-[(1R or 1S)-1-(5-{6-[(5-Fluoro-4-methylpyridin-2-yl)amino]pyridin-2-yl}-1,3-thiazol-2-yl)-1-hydroxyethyl]cyclohexanecarboxylic acid (Enantiomer 1)

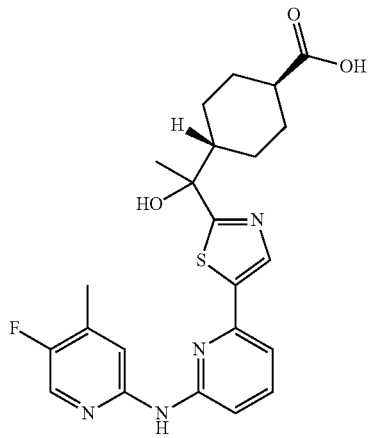 [SMILES: Cc1cc(Nc2cccc(-c3cnc(C(C)(O)[C@H]4CC[C@H](C(=O)O)CC4)s3)n2)ncc1F]

Step 1:
A solution of 5-fluoro-4-methylpyridin-2-amine (16.2 mg, 0.128 mmol), butyl trans-4-{1-[5-(6-bromopyridin-2-yl)-1,3-thiazol-2-yl]-1-hydroxyethyl}cyclohexanecarboxylate (Intermediate 4, Step 2, Enantiomer 1, R$_f$=3.98 min) (57 mg, 0.122 mmol), Xantphos (10.6 mg, 0.018 mmol), cesium carbonate (79 mg, 0.244 mmol), and palladium(II) acetate (2.7 mg, 0.012 mmol) in 1,4-dioxane (0.8 mL) under an argon atmosphere was heated to 115° C. for 1.5 hours. After cooling to room temperature, the reaction mixture was partitioned between ethyl acetate (20 mL) and saturated aqueous sodium bicarbonate solution (10 mL). The layers were separated and the organic layer was washed with brine, dried over sodium sulfate, filtered, and concentrated under reduced pressure. The residue was purified by chromatography on silica gel (25-45% ethyl acetate/hexanes) to provide butyl trans-4-[(1R or 1S)-1-(5-{6-[(5-fluoro-4-methylpyridin-2-yl)amino]pyridin-2-yl}-1,3-thiazol-2-yl)-1-hydroxyethyl]cyclohexanecarboxylate. MS ESI calc'd. for $C_{27}H_{33}FN_4O_3S$ [M+H]$^+$ 513. found 513. $^1$H NMR (500 MHz, CDCl$_3$) δ 8.10 (s, 1H), 8.01 (s, 1H), 7.88 (d, J=5.8 Hz, 1H), 7.60 (t, J=7.9 Hz, 1H), 7.20 (d, J=7.6 Hz, 1H), 7.17 (s, 1H), 7.07 (d, J=8.3 Hz, 1H), 4.04 (t, J=6.6 Hz, 2H), 3.03 (s, 1H), 2.38 (s, 3H), 2.24-2.17 (m, 1H), 2.10-1.98 (m, 3H), 1.83-1.75 (m, 1H), 1.73-1.67 (m, 1H), 1.65 (s, 3H), 1.62-1.56 (m, 2H), 1.48-1.38 (m, 2H), 1.40-1.32 (m, 2H), 1.32-1.25 (m, 1H), 1.23-1.15 (m, 1H), 0.91 (t, J=7.4 Hz, 3H).

Step 2:

To a solution of butyl trans-4-[(1R or 1S)-1-(5-{6-[(5-fluoro-4-methylpyridin-2-yl)amino]pyridin-2-yl}-1,3-thiazol-2-yl)-1-hydroxyethyl]cyclohexanecarboxylate (54.7 mg, 0.107 mmol) in tetrahydrofuran (0.6 mL) and methanol (1.2 mL) was added sodium hydroxide (1.0 M in water, 0.427 mL, 0.427 mmol). The reaction mixture was heated in a microwave oven for 5 minutes at 110° C. and then hydrochloric acid (2.0 M in water, 0.220 mL, 0.440 mmol) was added. The mixture was diluted with 10% IPA:CHCl$_3$ (25 mL), ethyl acetate (100 mL), and brine. The layers were separated and the organic layer was washed with brine, dried over sodium sulfate, filtered, and concentrated under reduced pressure to provide trans-4-[(1R or 1S)-1-(5-{6-[(5-fluoro-4-methylpyridin-2-yl)amino]pyridin-2-yl}-1,3-thiazol-2-yl)-1-hydroxyethyl]cyclohexanecarboxylic acid. MS ESI calc'd. for $C_{23}H_{25}FN_4O_3S$ [M+H]$^+$ 457. found 457. $^1$H NMR (500 MHz, DMSO-d$_6$) δ 11.95 (br s, 1H), 9.74 (s, 1H), 8.26 (s, 1H), 8.15 (d, J=6.1 Hz, 1H), 8.11 (s, 1H), 7.66 (t, J=7.9 Hz, 1H), 7.36 (d, J=7.3 Hz, 1H), 7.23 (d, J=8.2 Hz, 1H), 5.82 (s, 1H), 2.32 (s, 3H), 2.07-1.94 (m, 1H), 1.92-1.83 (m, 3H), 1.67-1.60 (m, 1H), 1.54-1.48 (m, 1H), 1.48 (s, 3H), 1.26-1.14 (m, 3H), 1.08-1.02 (m, 1H). rhSyk activity=+++.

Example 6 trans-4-[(1R or 1S)-1-(5-{6-[(5-Fluoro-4-methylpyridin-2-yl)amino]pyridin-2-yl}-1,3-thiazol-2-yl)-1-hydroxyethyl]cyclohexanecarboxylic acid (Enantiomer 2)

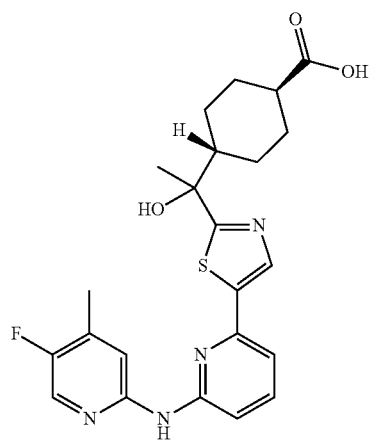

Step 1:

A solution of 5-fluoro-4-methylpyridin-2-amine (15.6 mg, 0.124 mmol), butyl trans-4-{(1R or 1S)-1-[5-(6-bromopyridin-2-yl)-1,3-thiazol-2-yl]-1-hydroxyethyl}cyclohexanecarboxylate (Intermediate 4, Step 2, Enantiomer 2, R$_t$=4.76 min) (55 mg, 0.118 mmol), Xantphos (10.2 mg, 0.018 mmol), cesium carbonate (77 mg, 0.235 mmol), and palladium(II) acetate (2.6 mg, 0.012 mmol) in 1,4-dioxane (0.8 mL) under an argon atmosphere was heated to 115° C. for 2 hours. After cooling to room temperature, the reaction mixture was partitioned between ethyl acetate (20 mL) and saturated aqueous sodium bicarbonate solution (10 mL). The layers were separated and the organic layer was washed with brine, dried over sodium sulfate, filtered, and concentrated under reduced pressure. The residue was purified by chromatography on silica gel (25-45% ethyl acetate/hexanes) to provide butyl trans-4-[(1R or 1S)-1-(5-{6-[(5-fluoro-4-methylpyridin-2-yl)amino]pyridin-2-yl}-1,3-thiazol-2-yl)-1-hydroxyethyl]cyclohexanecarboxylate. MS ESI calc'd. for $C_{27}H_{33}FN_4O_3S$ [M+H]$^+$ 513. found 513. $^1$H NMR (500 MHz, CDCl$_3$) δ 8.10 (s, 1H), 8.01 (s, 1H), 7.88 (d, J=5.7 Hz, 1H), 7.60 (t, J=7.9 Hz, 1H), 7.20 (d, J=7.5 Hz, 1H), 7.17 (s, 1H), 7.07 (d, J=8.2 Hz, 1H), 4.04 (t, J=6.7 Hz, 2H), 3.03 (s, 1H), 2.38 (s, 3H), 2.22-2.16 (m, 1H), 2.10-1.96 (m, 3H), 1.83-1.77 (m, 1H), 1.69-1.64 (m, 1H), 1.65 (s, 3H), 1.62-1.55 (m, 2H), 1.48-1.39 (m, 2H), 1.39-1.32 (m, 2H), 1.32-1.27 (m, 1H), 1.21-1.15 (m, 1H), 0.91 (t, J=7.4 Hz, 4H).

Step 2:

To a solution of butyl trans-4-[(1R or 1S)-1-(5-{6-[(5-fluoro-4-methylpyridin-2-yl)amino]pyridin-2-yl}-1,3-thiazol-2-yl)-1-hydroxyethyl]cyclohexanecarboxylate (48.5 mg, 0.095 mmol) in tetrahydrofuran (0.6 mL) and methanol (1.2 mL) was added sodium hydroxide (1.0 M in water, 0.378 mL, 0.378 mmol). The reaction mixture was heated in a microwave oven for 5 minutes at 110° C. and then hydrochloric acid (2.0 M in water, 0.192 mL, 0.384 mmol) was added. The resulting suspension was diluted with water and filtered to provide trans-4-[(1R or 1S)-1-(5-{6-[(5-fluoro-4-methylpyridin-2-yl)amino]pyridin-2-yl}hydroxyethyl]cyclohexanecarboxylic acid. MS ESI calc'd. for $C_{23}H_{25}FN_4O_3S$ [M+H]$^+$ 457. found 457. $^1$H NMR (500 MHz, DMSO-d$_6$) δ 11.95 (br s, 1H), 9.74 (s, 1H), 8.26 (s, 1H), 8.15 (d, J=5.7 Hz, 1H), 8.11 (s, 1H), 7.66 (t, J=7.9 Hz, 1H), 7.36 (d, J=7.4 Hz, 1H), 7.23 (d, J=8.5 Hz, 1H), 5.82 (s, 1H), 2.34 (s, 1H), 2.32 (s, 3H), 2.07-1.94 (m, 1H), 1.91-1.83 (m, 3H), 1.67-1.61 (m, 1H), 1.53-1.47 (m, 1H), 1.48 (s, 3H), 1.26-1.14 (m, 3H), 1.08-1.02 (m, 1H). rhSyk activity=+++.

Example 7 trans-4-{(1R or 1S)-1-Hydroxy-1-[5-(6-[4-(trifluoromethyl)pyridin-2-yl]amino pyridin-2-yl)-1,3-thiazol-2-yl]ethyl}cyclohexanecarboxylic acid (Enantiomer 1)

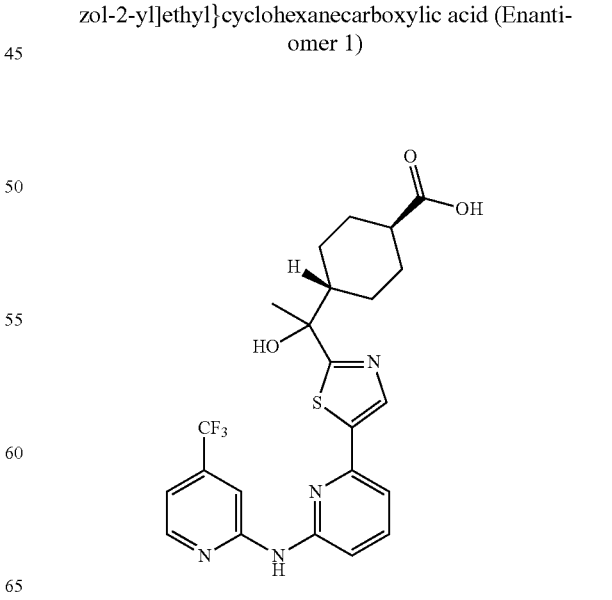

Step 1:

A solution of 4-(trifluoromethyl)pyridin-2-amine (20.8 mg, 0.128 mmol), butyl trans-4-{(1R or 1S)-1-[5-(6-bromopyridin-2-yl)-1,3-thiazol-2-yl]-1-hydroxyethyl}-cyclohexanecarboxylate (Intermediate 4, Step 2, Enantiomer 1, R$_t$=3.98 min) (57 mg, 0.122 mmol), Xantphos (10.6 mg, 0.018 mmol), cesium carbonate (79 mg, 0.244 mmol), and palladium(II) acetate (2.7 mg, 0.012 mmol) in 1,4-dioxane (0.8 mL) under an argon atmosphere was heated to 115° C. for 2 hours. After cooling to room temperature, the reaction mixture was partitioned between ethyl acetate (20 mL) and saturated aqueous sodium bicarbonate solution (10 mL). The layers were separated and the organic layer was washed with brine, dried over sodium sulfate, filtered, and concentrated under reduced pressure. The residue was purified by chromatography on silica gel (25-45% ethyl acetate/hexanes) to provide butyl trans-4-{(1R or 1S)-1-hydroxy-1-[5-(6-{[4-(trifluoromethyl)pyridin-2-yl]amino}pyridin-2-yl)-1,3-thiazol-2-yl]ethyl}cyclohexanecarboxylic acid. MS ESI calc'd. for $C_{27}H_{31}F_3N_4O_3S$ [M+H]$^+$ 549. found 549. $^1$H NMR (500 MHz, CDCl$_3$) δ 8.61 (s, 1H), 8.41 (d, J=5.2 Hz, 1H), 8.10 (s, 1H), 7.65 (t, J=7.9 Hz, 1H), 7.48 (s, 1H), 7.28 (d, J=7.5 Hz, 1H), 7.11 (d, J=4.9 Hz, 1H), 6.94 (d, J=8.2 Hz, 1H), 4.04 (t, J=6.6 Hz, 2H), 3.20 (s, 1H), 2.22-2.16 (m, 1H), 2.10-1.98 (m, 3H), 1.79 (m, 1H), 1.69-1.64 (m, 1H), 1.65 (s, 3H), 1.62-1.57 (m, 3H), 1.49-1.39 (m, 2H), 1.38-1.33 (m, 1H), 1.32-1.24 (m, 1H), 1.21-1.18 (m, 1H), 0.91 (t, J=7.4 Hz, 3H).

Step 2:

To a solution of butyl trans-4-{(1R or 1S)-1-hydroxy-1-[5-(6-{[4-(trifluoromethyl)pyridin-2-yl]amino}pyridin-2-yl)-1,3-thiazol-2-yl]ethyl}cyclohexanecarboxylic acid (59.6 mg, 0.109 mmol) in tetrahydrofuran (0.6 mL) and methanol (1.2 mL) was added sodium hydroxide (1.0 M in water, 0.435 mL, 0.435 mmol). The reaction mixture was heated in a microwave oven for 5 minutes at 110° C. and then hydrochloric acid (2.0 M in water, 0.220 mL, 0.440 mmol) was added. The resulting mixture was diluted with 10% IPA:CHCl$_3$ and brine and the layers were separated. The aqueous layer was extracted with 10% IPA:CHCl$_3$ and then the combined organic layers were dried over sodium sulfate, filtered, and concentrated under reduced pressure to afford trans-4-{(1R or 1S)-1-hydroxy-1-[5-(6-{[4-(trifluoromethyl)pyridin-2-yl]amino}pyridin-2-yl)-1,3-thiazol-2-yl]ethyl}cyclohexanecarboxylic acid. MS ESI calc'd. for $C_{23}H_{23}F_3N_4O_3S$ [M+H]$^+$ 493. found 493. $^1$H NMR (500 MHz, DMSO-d$_6$) δ 11.95 (s, 1H), 10.27 (s, 1H), 8.64 (s, 1H), 8.49 (d, J=5.2 Hz, 1H), 8.28 (s, 1H), 7.73 (t, J=7.9 Hz, 1H), 7.46 (d, J=7.5 Hz, 1H), 7.26 (d, J=8.2 Hz, 1H), 7.22 (d, J=5.2 Hz, 1H), 5.75 (d, J=10.1 Hz, 1H), 2.01 (m, 1H), 1.94-1.82 (m, 2H), 1.64 (m, 1H), 1.53 (m, 1H), 1.48 (s, 3H), 1.24-1.14 (m, 4H), 1.02 (m, 1H). rhSyk activity=+++.

Example 8 trans-4-{(1R or 1S)-1-Hydroxy-1-[5-(6-{[4-(trifluoromethyl)pyridin-2-yl]amino}pyridin-2-yl)-1,3-thiazol-2-yl]ethyl}cyclohexanecarboxylic acid (Enantiomer 2)

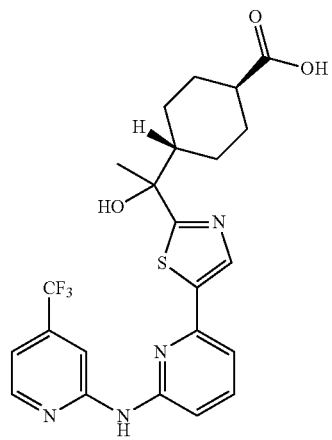 [SMILES: CC(O)(c1ncc(-c2cccc(Nc3cc(C(F)(F)F)ccn3)n2)s1)[C@H]1CC[C@H](C(=O)O)CC1]

Step 1:

A solution of 4-(trifluoromethyl)pyridin-2-amine (20.0 mg, 0.124 mmol), butyl trans-4-{(1R or 1S)-1-[5-(6-bromopyridin-2-yl)-1,3-thiazol-2-yl]-1-hydroxyethyl}cyclohexanecarboxylate (Intermediate 4, Step 2, Enantiomer 2, R$_t$=4.76 min) (55 mg, 0.118 mmol), XANTPHOS (10.2 mg, 0.018 mmol), cesium carbonate (77 mg, 0.235 mmol), and palladium(II) acetate (2.6 mg, 0.012 mmol) in 1,4-dioxane (0.8 mL) under an argon atmosphere was heated to 115° C. for 2 hours. After cooling to room temperature, the reaction mixture was partitioned between ethyl acetate (20 mL) and saturated aqueous sodium bicarbonate solution (10 mL). The layers were separated and the organic layer was washed with brine, dried over sodium sulfate, filtered, and concentrated under reduced pressure. The residue was purified by chromatography on silica gel (25-45% ethyl acetate/hexanes) to provide butyl trans-4-{(1R or 1S)-1-Hydroxy-1-[5-(6-{[4-(trifluoromethyl)pyridin-2-yl]amino}pyridin-2-yl)-1,3-thiazol-2-yl]ethyl}cyclohexanecarboxylic acid. MS ESI calc'd. for $C_{27}H_{31}F_3N_4O_3S$ [M+H]$^+$ 549. found 549. $^1$H NMR (500 MHz, CDCl$_3$) δ 8.61 (s, 1H), 8.41 (d, J=4.7 Hz, 1H), 8.10 (s, 1H), 7.65 (t, J=7.9 Hz, 1H), 7.47 (s, 1H), 7.28 (d, J=7.0 Hz, 1H), 7.11 (d, J=4.3 Hz, 1H), 6.94 (d, J=8.1 Hz, 1H), 4.04 (t, J=6.6 Hz, 2H), 3.20 (s, 1H), 2.22-2.17 (m, 1H), 2.10-1.98 (m, 3H), 1.82-1.76 (m, 1H), 1.70-1.65 (m, 1H), 1.65 (s, 3H), 1.62-1.57 (m, 3H), 1.48-1.39 (m, 2H), 1.38-1.33 (m, 1H), 1.32-1.24 (m, 1H), 1.20-1.14 (m, 1H), 0.91 (t, J=7.4 Hz, 3H).

Step 2:

To a solution of butyl trans-4-{(1R or 1S)-1-hydroxy-1-[5-(6-{[4-(trifluoromethyl)pyridin-2-yl]amino}pyridin-2-yl)-1,3-thiazol-2-yl]ethyl}cyclohexanecarboxylic acid (58.5 mg, 0.107 mmol) in tetrahydrofuran (0.6 mL) and methanol (1.2 mL) was added sodium hydroxide (1.0 M in water, 0.427 mL, 0.427 mmol). The reaction mixture was heated in a microwave oven for 5 minutes at 110° C. and then hydrochloric acid (2.0 M in water, 0.215 mL, 0.430 mmol) was added. The resulting mixture was diluted with 10% IPA:CHCl₃ and brine and the layers were separated. The aqueous layer was extracted with 10% IPA:CHCl₃ and then the combined organic layers were dried over sodium sulfate, filtered, and concentrated under reduced pressure to afford trans-4-{(1R or 1S)-1-hydroxy-1-[5-(6-{[4-(trifluoromethyl)pyridin-2-yl]amino}pyridin-2-yl)-1,3-thiazol-2-yl]ethyl}cyclohexanecarboxylic acid. MS ESI calc'd. for $C_{23}H_{23}F_3N_4O_3S$ $[M+H]^+$ 493. found 493. $^1H$ NMR (500 MHz, DMSO-d₆) δ 11.95 (br s, 1H), 10.27 (s, 1H), 8.64 (s, 1H), 8.49 (d, J=5.1 Hz, 1H), 8.28 (s, 1H), 7.73 (t, J=7.9 Hz, 1H), 7.46 (d, J=7.5 Hz, 1H), 7.26 (d, J=8.2 Hz, 1H), 7.22 (d, J=5.3 Hz, 1H), 5.76 (s, 1H), 2.02-1.95 (m, 1H), 1.94-1.92 (m, 2H), 1.66-1.61 (m, 1H), 1.54-1.49 (m, 1H), 1.48 (s, 3H), 1.24-1.14 (m, 4H), 1.05-0.99 (m, 1H). rhSyk activity=+++.

Example 9

Butyl trans-4-[(1R)-1-(5-{6-[(5-fluoro-4-methylpyridin-2-yl)amino]-4-methylpyridin-2-yl}-1,3-thiazol-2-yl)-1-hydroxyethyl]cyclohexanecarboxylate and butyl trans-4-[(1S)-1-(5-{6-[(5-fluoro-4-methylpyridin-2-yl)amino]-4-methylpyridin-2-yl}-1,3-thiazol-2-yl)-1-hydroxyethyl]cyclohexanecarboxylate

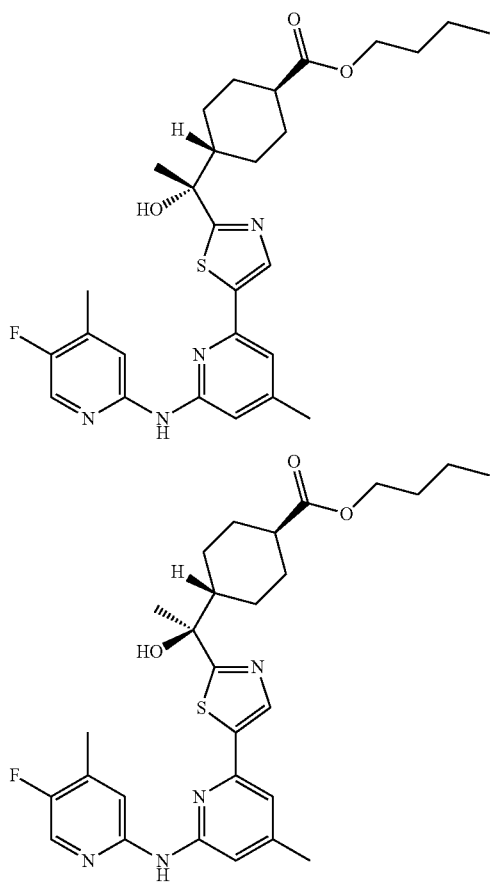

Step 1:
Into a flask were added 2,6 dibromo-4-methyl pyridine (10.0 g, 40.0 mmol), sodium tert-butoxide (4.4 g, 46.0 mmol), 2-amino-4-methyl-5-fluoro pyridine (5.8 g, 45.8 mmol) and 1,1'-bis(di-tert-butylphosphino)ferrocene palladium dichloride (1.3 g, 1.9 mmol) followed by nitrogen sparged 1,4-dioxane (100 mL). The slurry was evacuated and refilled with nitrogen three times and then heated to 88° C. for 5 hours. After cooling to 25° C., ethyl acetate (100 mL) and water (20 mL) were added and the layers were separated. The organic layer was washed with 10% aqueous sodium chloride solution (25 mL) and then concentrated under reduced pressure. The residue was purified by chromatography on silica gel (10-50% ethyl acetate/hexanes) to afford N-(6-bromo-4-methylpyridine-2-yl)-5-fluoro-4-methylpyridine-2-amine. $^1H$ NMR (600 MHz, DMSO-d₆) δ 9.87 (s, 1H), 8.07 (d, J=0.8 Hz, 1H), 7.61 (s, 1H), 7.32 (d, J=5.6 Hz, 1H), 6.87 (s, 1H), 2.20 (s, 3H), 2.19 (s, 3H).

Step 2:
Into a flask were added butyl diadamantyl phosphine (0.133 g, 0.37 mmol), palladium(II) acetate (0.04 g, 2.2 mmol), potassium carbonate (0.77 g, 5.6 mmol), pivalic acid (0.23 g, 2.2 mmol), butyl trans-4-[1-hydroxy-1-(1,3-thiazol-2-yl)ethyl]cyclohexanecarboxylate (0.69 g, 60.0 mmol), and N-(6-bromo-4-methylpyridine-2-yl)-5-fluoro-4-methylpyridine-2-amine (0.55 g, 1.86 mmol) followed by nitrogen sparged dimethyl acetamide (4.4 mL). The slurry was evacuated and refilled with nitrogen three times and then slowly heated to 130° C. for 15 hours. The slurry was cooled to 35° C. and diluted with ethyl acetate (100 mL). The slurry was then filtered through CELITE, washed with 10% aqueous NaCl (3×100 mL) and concentrated under reduced pressure. The residue was purified by chromatography on silica gel (ethyl acetate/hexanes) to obtain racemic butyl trans-4-[1-(5-{6-[(5-fluoro-4-methylpyridine-2-yl)amino]-4-methylpyridine-2-yl}-1,3-thiazol-2-yl)-1-hydroxyethyl]cyclohexanecarboxylate as a foam. $^1H$ NMR (600 MHz, DMSO-d₆) δ 9.62 (s, 1H), 8.21 (s, 1H), 8.12 (d, J=5.8 Hz, 1H), 8.08 (s, 1H), 7.21 (s, 1H), 7.04 (s, 1H), 5.79 (s, 1H), 3.93 (t, J=6.5 Hz, 2H), 2.29 (s, 3H), 2.25 (s, 3H), 2.14-2.05 (m, 1H), 1.93-1.80 (m, 3H), 1.65-1.60 (m, 1H), 1.53-1.47 (m, 3H), 1.45 (s, 3H), 1.31-1.16 (m, 5H), 1.08-0.99 (m, 1H), 0.83 (t, J=7.4 Hz, 3H).

Two enantiomers were separated by chiral super critical fluid chromatography (Chiral Technology AS-H, 2.1×25 cm, 5 uM, 20/80 ethanol/CO₂, Flow Rate: 70 mL/min, 11 min run time, WL: 275 nm). Elution was observed at 5.77 min and 7.36 min. Pooled fractions of each peak were concentrated under reduced pressure.

Enantiomer 1 (retention time=5.77 min): MS ESI calc'd. for $C_{28}H_{35}FN_4O_3S$ $[M+H]^+$ 527. found 527. $^1H$ NMR (500 MHz, DMSO-d₆) δ 9.65 (s, 1H), 8.24 (s, 1H), 8.15 (d, J=5.9 Hz, 1H), 8.10 (s, 1H), 7.24 (s, 1H), 7.06 (s, 1H), 5.82 (s, 1H), 3.96 (t, J=6.5 Hz, 2H), 2.31 (s, 3H), 2.27 (s, 3H), 2.14-2.08 (m, 1H), 1.95-1.80 (m, 3H), 1.68-1.63 (m, 1H), 1.57-1.48 (m, 3H), 1.48 (s, 3H), 1.33-1.14 (m, 5H), 1.08-1.01 (m, 1H), 0.85 (t, J=7.4 Hz, 3H). rhSyk activity=++

Enantiomer 2 (retention time=7.36 min) MS ESI calc'd. for $C_{28}H_{35}FN_4O_3S$ [M+H]$^+$ 527. found 527. $^1$H NMR (500 MHz, DMSO-d$_6$) δ 9.65 (s, 1H), 8.24 (s, 1H), 8.14 (d, J=5.7 Hz, 1H), 8.10 (s, 1H), 7.24 (s, 1H), 7.06 (s, 1H), 5.82 (s, 1H), 3.96 (t, J=6.5 Hz, 2H), 2.31 (s, 3H), 2.27 (s, 3H), 2.11 (s, 1H), 1.95-1.80 (m, 3H), 1.68-1.63 (m, 1H), 1.57-1.48 (m, 3H), 1.48 (s, 3H), 1.33-1.17 (m, 5H), 1.05 (m, 1H), 0.85 (t, J=7.4 Hz, 3H). rhSyk activity=++

Example 10 trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid (Enantiomer 1)

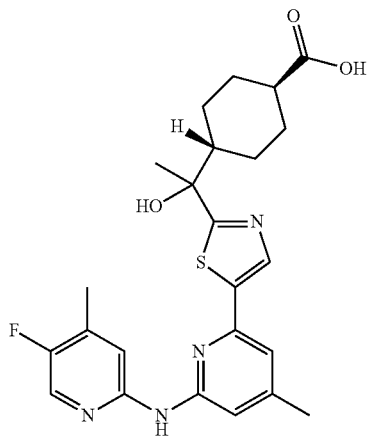 [SMILES: Cc1cc(Nc2cc(C)c(F)cn2)nc(-c2cnc(C(C)(O)[C@H]3CC[C@H](C(=O)O)CC3)s2)c1]

To a solution of butyl trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylate (Example 9, Step 2, Enantiomer 1, R$_t$=5.77 min) (725 mg, 1.377 mmol) in tetrahydrofuran (8 mL) and methanol (16 mL) was added sodium hydroxide (1.0 M in water, 5.51 mL, 5.51 mmol). The reaction mixture was heated to 70° C. for 90 minutes and then allowed to cool to room temperature. Hydrochloric acid (2.0 M in water, 2.75 mL, 5.50 mmol) and water (30 mL) were added and the resulting precipitate was collected by filtration. The solid was washed with water (2×10 mL) and then dried under reduced pressure to give trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylate. MS ESI calc'd. for $C_{24}H_{27}FN_4O_3S$ [M+H]$^+$ 471. found 471. $^1$H NMR (500 MHz, DMSO-d$_6$) δ 11.96 (br s, 1H), 9.65 (s, 1H), 8.24 (s, 1H), 8.14 (d, J=6.0 Hz, 1H), 8.10 (s, 1H), 7.24 (s, 1H), 7.06 (s, 1H), 5.81 (s, 1H), 2.31 (s, 3H), 2.27 (s, 3H), 2.04-1.98 (m, 1H), 1.94-1.82 (m, 3H), 1.66-1.61 (m, 1H), 1.53-1.48 (m, 1H), 1.48 (s, 3H), 1.28-1.14 (m, 3H), 1.07-1.02 (m, 1H). rhSyk activity=+++.

Example 11 trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylic acid (Enantiomer 2)

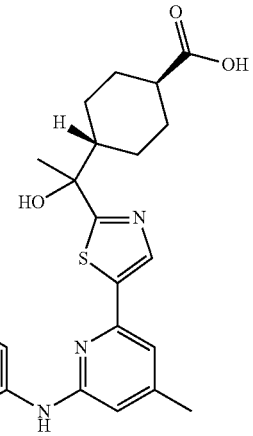

To a solution of butyl trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylate (Example 9, Step 2, Enantiomer 2, R$_t$=7.36 min) (725 mg, 1.377 mmol) in tetrahydrofuran (8 mL) and methanol (16 mL) was added sodium hydroxide (1.0 M in water, 5.51 mL, 5.51 mmol). The reaction mixture was heated to 70° C. for 90 minutes and then allowed to cool to room temperature. Hydrochloric acid (2.0 M in water, 2.75 mL, 5.50 mmol) and water (30 mL) were added and the resulting precipitate was collected by filtration. The solid was washed with water (2×10 mL) and then dried under reduced pressure to give trans-4-[(1R or 1S)-1-(5-{6-[(5-fluoro-4-methylpyridine-2-yl)amino]-4-methylpyridine-2-yl}-1,3-thiazol-2-yl)-1-hydroxyethyl]cyclohexanecarboxylate. MS ESI calc'd. for $C_{24}H_{27}FN_4O_3S$ [M+H]$^+$ 471. found 471. $^1$H NMR (500 MHz, DMSO-d$_6$) δ 11.96 (br s, 1H), 9.65 (s, 1H), 8.24 (s, 1H), 8.14 (d, J=6.0 Hz, 1H), 8.10 (s, 1H), 7.24 (s, 1H), 7.06 (s, 1H), 5.81 (s, 1H), 2.31 (s, 3H), 2.27 (s, 3H), 2.04-1.98 (m, 1H), 1.94-1.82 (m, 3H), 1.66-1.61 (m, 1H), 1.53-1.48 (m, 1H), 1.48 (s, 3H), 1.28-1.14 (m, 3H), 1.07-1.02 (m, 1H). rhSyk activity=+++.

Example 12

1-[5-(4-Methyl-6-{[4-(trifluoromethyl)pyridin-2-yl]amino}pyridin-2-yl)-1,3-thiazol-2-yl]-1-(pyrrolidin-3-yl)ethanol

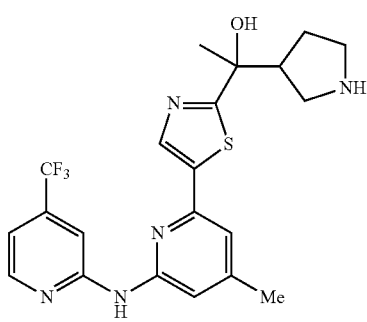 [SMILES: Cc1cc(Nc2cc(C(F)(F)F)ccn2)nc(-c2cnc(C(C)(O)C3CCNC3)s2)c1]

Step 1:

Isopropylmagnesium chloride lithium chloride (1.3 M in tetrahydrofuran, 0.6 mL, 0.780 mmol) was added dropwise at room temperature to a flask containing a solution of thiazole (0.050 mL, 0.705 mmol) in tetrahydrofuran (5 mL) with a water bath around the flask. After 40 min, tert-butyl 3-acetylpyrrolidine-1-carboxylate (160 mg, 0.750 mmol) in tetrahydrofuran (5 mL) was added dropwise. After stirring at room temperature for 35 min, the mixture was diluted with saturated aqueous ammonium chloride and extracted with ethyl acetate. The organic phase was washed with water and brine, dried over sodium sulfate, and concentrated under reduced pressure. The residue was purified by chromatography on silica gel (0-60% ethyl acetate/hexane) to afford tert-butyl 3-[1-hydroxy-1-(1,3-thiazol-2-yl)ethyl]pyrrolidine-1-carboxylate as a 1:1 mix of diastereomers. $^1$H NMR (500 MHz, CDCl$_3$) δ 7.69-7.55 (m, 1H, two sets of doublets overlap from two diastereomers), 7.23-7.14 (m, 1H, two sets of doublets overlap from two diastereomers), 3.59-2.98 (m, 4H), 2.80-2.60 (m, 1H), 1.98-1.70 (m, 2H), 1.59 (s, 3H), 1.45-1.30 (m, 9H, two sets of peaks overlap from two diastereomers).

Step 2:

tert-Butyl 3-[1-hydroxy-1-(1,3-thiazol-2-yl)ethyl]pyrrolidine-1-carboxylate (100 mg, 0.335 mmol), 6-bromo-4-methyl-N-[4-(trifluoromethyl)pyridin-2-yl]pyridin-2-amine (112 mg, 0.337 mmol), butyl di-1-adamantylphosphine (25 mg, 0.070 mmol), tris(dibenzylideneacetone)dipalladium(0) (16.3 mg, 0.018 mmol), pivalic acid (0.018 mL, 0.157 mmol), potassium carbonate (140 mg, 1.013 mmol) and N,N-dimethylacetamide (1 mL) were combined and the mixture was evacuated and purged with nitrogen 3 times then heated to 130° C. for 7 hours. The mixture was filtered then extracted with ethyl acetate. The organic phase was washed with water and brine, dried over sodium sulfate, and concentrated under reduced pressure to afford tert-butyl 3-{1-hydroxy-1-[5-(4-methyl-6-{[4-(trifluoromethyl)-pyridin-2-yl]amino}pyridin-2-yl)-1,3-thiazol-2-yl]ethyl}pyrrolidine-1-carboxylate, which was used in a subsequent step without further purification. MS ESI calc'd. for C$_{26}$H$_{30}$F$_3$N$_5$O$_3$S [M+H]$^+$ 550. found 550.

Step 3:

Trifluoroacetic acid (0.4 mL, 5.19 mmol) was added to a solution of tert-butyl 3-{1-hydroxy-1-[5-(4-methyl-6-{[4-(trifluoromethyl)pyridin-2-yl]amino}pyridin-2-yl)-1,3-thiazol-2-yl]ethyl}pyrrolidine-1-carboxylate (100 mg, 0.182 mmol) in dichloromethane (0.8 mL). The mixture was stirred at room temperature for 16 hours then concentrated under reduced pressure. The residue was purified on reverse phase HPLC (Sunfire prep C18 OBD 5 uM, acetonitrile/water+0.1% TFA) to afford 1-[5-(4-methyl-6-{[4-(trifluoromethyl)pyridin-2-yl]amino}pyridin-2-yl)-1,3-thiazol-2-yl]-1-(pyrrolidin-3-yl)ethanol as a 1:1 mix of diastereomers. MS ESI calc'd. for C$_{21}$H$_{22}$F$_3$N$_5$OS [M+H]$^+$ 450. found 450. $^1$H NMR (500 MHz, CD$_3$OD) δ 8.55 (d, J=5.6 Hz, 1H), 8.37 (d, 11-1, two singlets from two diastereomers), 8.12 (s, 1H), 7.46 (s, 1H), 7.37 (d, J=5.5 Hz, 1H), 7.05 (s, 1H), 3.58-2.95 (m, 5H, two sets of peaks from two diastereomers), 2.45 (s, 3H), 2.30-1.79 (m, 2H, two sets of peaks from two diastereomers), 1.69 (d, 3H, two singlets from two diastereomers). rhSyk activity=+++.

Example 13

3-{1-Hydroxy-1-[5-(4-methyl-6-{[4-(trifluoromethyl)pyridin-2-yl]amino}pyridin-2-yl)-1,3-thiazol-2-yl]ethyl}pyrrolidine-1-carboxamide

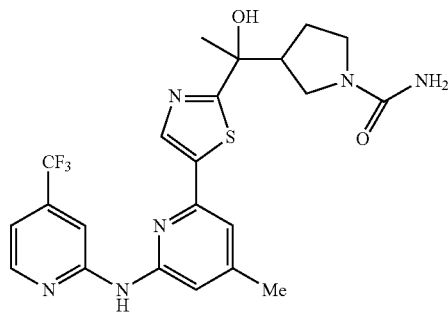 [SMILES: Cc1cc(Nc2cc(C(F)(F)F)ccn2)nc(-c2cnc(C(C)(O)C3CCN(C(N)=O)C3)s2)c1]

To the solution of 1-[5-(4-methyl-6-{[4-(trifluoromethyl)pyridin-2-yl]amino}pyridin-2-yl)-1,3-thiazol-2-yl]-1-(pyrrolidin-3-yl)ethanol (20 mg, 0.044 mmol, 1:1 mix of diastereomers) in tetrahydrofuran (0.4 mL) was added potassium cyanate (25 mg, 0.308 mmol), water (1.2 mL) and HCl (2 M in water, 0.14 mL, 0.280 mmol). The mixture was stirred at 55° C. for 3 hours then cooled to room temperature. The mixture was purified on reversed phase HPLC (Sunfire prep C18 OBD 5 uM, acetonitrile/water+0.1% TFA) to afford 3-{1-hydroxy-1-[5-(4-methyl-6-{[4-(trifluoromethyl)pyridin-2-yl]amino}pyridin-2-yl)-1,3-thiazol-2-yl]

ethyl}pyrrolidine-1-carboxamide as a 1:1 mixture of diastereomers. MS ESI calc'd. for $C_{22}H_{23}F_3N_6O_2S$ [M+H]$^+$ 493. found 493. $^1$H NMR (500 MHz, CD$_3$OD) δ 8.65-8.60 (m, 1H, two sets of doublets overlap from two diastereomers), 8.39 (d, 1H, two singlets from two diastereomers), 7.86 (s, 1H), 7.51 (d, 1H, two singlets from two diastereomers), 7.46-7.42 (m, 1H, two sets of doublets overlap from two diastereomers), 7.05 (s, 1H), 3.65-2.82 (m, 5H, two sets of peaks from two diastereomers), 2.50 (s, 3H), 2.20-2.00 (m, 2H), 1.69 (s, 3H). rhSyk activity=+++.

Example 14

Alternative Preparation of Examples 4 and 3; Preparation of Related Compounds of Formula I trans-4-{(1R or 1S)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid (Enantiomer 1, same stereoisomer as Example 4)

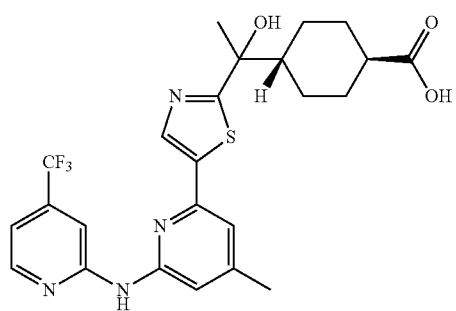 [SMILES: Cc1cc(Nc2cc(C(F)(F)F)ccn2)nc(-c2cnc(C(C)(O)[C@H]3CC[C@H](C(=O)O)CC3)s2)c1]

Step 1:
To a vial under nitrogen was added palladium acetate (10 mg, 0.045 mmol), butyl di-1-adamantylphosphine (32 mg, 0.090 mmol) and dioxane (1 mL) and the mixture was stirred for 10 minutes. To a separate flask was added 6-bromo-4-methyl-N-(4-(trifluoromethyl)pyridin-2-yl)pyridin-2-amine (75 mg, 0.23 mmol), cesium fluoride (103 mg, 0.68 mmol), pivalic acid (35 mg, 0.34 mmol) and a solution of butyl trans-4-[(1R or 1S)-1-hydroxy-1-(1,3-thiazol-2-yl)ethyl]cyclohexanecarboxylate (Intermediate 2, Peak 2, R$_f$=4.14 min) (70 mg, 0.23 mmol) in dioxane (1 mL). The mixture in flask 1 was added to the mixture in flask 2 and the resulting mixture was evacuated and then purged 5 times with argon. The mixture was then heated to 100° C. for 24 hours. The mixture was then diluted with ethyl acetate, filtered through CELITE and the CELITE was washed with ethyl acetate. The filtrate was concentrated in vacuo and the crude product was purified by chromatography on silica gel to afford butyl trans-4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylate. MS ESI calc'd. for $C_{28}H_{34}F_3N_4O_3S$ [M+H]$^+$ $^{563}$. found 563. $^1$H NMR (500 MHz, DMSO-d$_6$) δ 10.18 (s, 1H), 8.65 (s, 1H), 8.48 (d, J=5.1 Hz, 1H), 7.34 (s, 1H), 7.19 (t, J=12.4 Hz, 1H), 7.06 (d, J=16.9 Hz, 1H), 5.76 (s, 1H), 3.95 (t, J=6.5 Hz, 2H), 2.31 (s, 3H), 2.17-2.05 (m, 1H), 1.96-1.80 (m, 3H), 1.72-1.59 (m, 1H), 1.59-1.44 (m, 5H), 1.35-1.14 (m, 6H), 1.11-0.96 (m, 1H), 0.84 (t, J=7.4 Hz, 3H). rhSyk=++

Step 2:
To a microwave vial containing butyl trans-4-{(1R or 1S)-1-hydroxy-1-[5-(4-methyl-6-{[4-(trifluoromethyl)pyridin-2-yl]amino}pyridin-2-yl)-1,3-thiazol-2-yl]ethyl}cyclohexanecarboxylate (76 mg, 0.14 mmol) in methanol (3 mL) was added aqueous sodium hydroxide (1 M in water, 2.0 mL, 2.0 mmol) and the mixture was heated in the microwave at 140° C. for 60 minutes. The mixture was allowed to cool to room temperature and acidified with aqueous hydrochloric acid to a pH 3. The mixture was diluted with ethyl acetate and the organic layer was separated, dried over magnesium sulfate, filtered and concentrated to afford trans-4-{(1R or 1S)-1-Hydroxy-1-[5-(4-methyl-6-{[4-(trifluoromethyl)pyridin-2-yl]amino}pyridin-2-yl)-1,3-thiazol-2-yl]ethyl}cyclohexanecarboxylic acid (Enantiomer 1). MS ESI calc'd. for $C_{24}H_{26}F_3N_4O_3S$ [M+H]$^+$ 507. found 507. $^1$H NMR (500 MHz, CD$_3$OD) δ 8.62 (d, J=5.6 Hz, 1H), 8.38 (s, 1H), 7.92 (s, 1H), 7.51 (s, 1H), 7.40 (t, J=16.4 Hz, 1H), 7.05 (s, 1H), 2.50 (s, 3H), 2.24-2.11 (m, 1H), 2.10-1.93 (m, 3H), 1.89-1.76 (m, 1H), 1.66-1.58 (m, 4H), 1.47-1.31 (m, 3H), 1.26-1.11 (m, 1H). rhSyk=+++

The following compounds were prepared in an analogous manner of that described in Example 14, step 1, and where appropriate, step 2 as well. Unless otherwise specified, the terms cis and trans refer to the stereochemistry around the cycloalkyl ring.

For compounds 3, compounds 14-1 through 14-10, compounds 14-39 through 14-43 and compounds 14-52 through 14-54, Enantiomer 1 was prepared from Intermediate 2, Peak 2 while Enantiomer 2 was prepared from Intermediate 2, Peak 1.

For compounds 14-30 through 14-38 and 14-44 through 14-51, Isomer 1 was prepared from Intermediate 13, Step 3, Peak 1 while Isomer 2 was prepared from Intermediate 13, Step 3, Peak 2. Compound 14-30 was prepared from the diastereomeric mixture from Intermediate 13, Step 4. Compounds 14-11 through 14,14 were prepared from Intermediate 12. Compounds 14-15, 14-16, 14-21 and 14-22 were prepared from Example 1, Step 2. Compounds 14-17, 14-18, 14-23 and 14-24 were prepared from Intermediate 8. Compounds 14-19, 14-20, 14-25 and 14-26 were prepared from Intermediate 9. Compounds 14-27 through 14-29 were prepared from Intermediate 10. Compound 14-55 was prepared from Intermediate 15, Step 2. Compound 14-56 was prepared from Intermediate 15, Step 3.

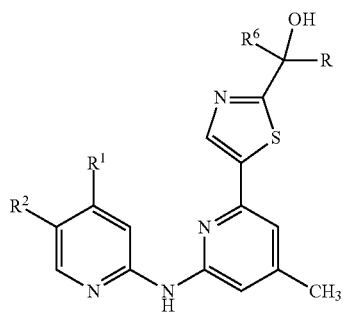

| Ex. | $R^1/R^2$ | $R^6$ | R | rhSyk Activity | [M + H]+ Obs'd | Form(s) |
|---|---|---|---|---|---|---|
| 3 | $CF_3$/H | $CH_3$ | cyclohexyl-$CO_2H$ (trans isomer, enantiomer 2) | +++ | 507 | Free Base |
| 14-1 | $CH_3$/H | $CH_3$ | cyclohexyl-$CO_2H$ (trans isomer, enantiomer 1) | +++ | 453 | Free Base |
| 14-2 | $OCH_3$/H | $CH_3$ | cyclohexyl-$CO_2$n-Bu (trans isomer, enantiomer 1) | ++ | 511 | Free Base |
| 14-3 | $OCH_3$/H | $CH_3$ | cyclohexyl-$CO_2H$ (trans isomer, enantiomer 1) | +++ | 469 | Free Base |
| 14-4 | $CHF_2$/H | $CH_3$ | cyclohexyl-$CO_2H$ (trans isomer, enantiomer 1) | +++ | 489 | TFA Salt |
| 14-5 | $CH_3$/Cl | $CH_3$ | cyclohexyl-$CO_2H$ (trans isomer, enantiomer 1) | +++ | 487 | Free Base |
| 14-6 | cPr/H | $CH_3$ | cyclohexyl-$CO_2$n-Bu (trans isomer, enantiomer 1) | ++ | 535 | Free Base |
| 14-7 | cPr/H | $CH_3$ | cyclohexyl-$CO_2H$ (trans isomer, enantiomer 1) | +++ | 479 | Free Base |

-continued

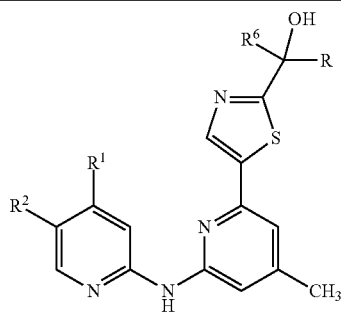

| Ex. | R¹/R² | R⁶ | R | rhSyk Activity | [M + H]+ Obs'd | Form(s) |
|---|---|---|---|---|---|---|
| 14-8 | iPr/H | CH₃ | cyclohexyl-CO₂H (trans isomer, enantiomer 1) | +++ | 481 | Free Base |
| 14-9 | Me/F | CH₃ | cyclohexyl-CO₂H (trans isomer, enantiomer 1) | +++ | 471 | Free Base |
| 14-10 | Me/F | CH₃ | cyclohexyl-CO₂H (trans isomer, enantiomer 2) | +++ | 471 | Free Base |
| 14-11 | CF₃/H | CH₃ | cyclopentyl-CO₂H (Isomer 1) | +++ | 493 | Free Base |
| 14-12 | CF₃/H | CH₃ | cyclopentyl-CO₂H (Isomer 2) | +++ | 493 | Free Base |
| 14-13 | CF₃/H | CH₃ | cyclopentyl-CO₂H (Isomer 3) | +++ | 493 | Free Base |
| 14-14 | CF₃/H | CH₃ | cyclopentyl-CO₂H (Isomer 4) | +++ | 493 | Free Base |
| 14-15 | CF₃/H | Et | cyclohexyl-CO₂H (trans isomer, enantiomer 1) | +++ | 521 | HCl Salt |

-continued

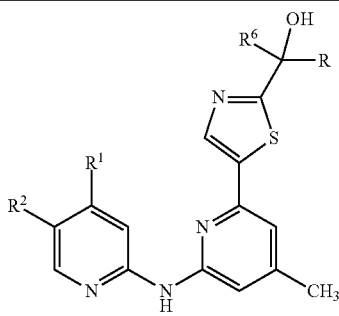

| Ex. | R¹/R² | R⁶ | R | rhSyk Activity | [M + H]+ Obs'd | Form(s) |
|---|---|---|---|---|---|---|
| 14-16 | CF₃/H | Et | cyclohexyl-CO₂H (trans isomer, enantiomer 2) | +++ | 521 | HCl Salt |
| 14-17 | CF₃/H | cPr | cyclohexyl-CO₂H (trans isomer, enantiomer 1) | +++ | 533 | TFA Salt |
| 14-18 | CF₃/H | cPr | cyclohexyl-CO₂H (trans isomer, enantiomer 2) | +++ | 533 | HCl Salt |
| 14-19 | CF₃/H | CF₃ | cyclohexyl-CO₂H (trans isomer, enantiomer 1) | +++ | 561 | HCl Salt |
| 14-20 | CF₃/H | CF₃ | cyclohexyl-CO₂H (trans isomer, enantiomer 2) | +++ | 561 | HCl Salt |
| 14-21 | OiPr/H | Et | cyclohexyl-CO₂H (trans isomer, enantiomer 1) | +++ | 511 | HCl Salt |
| 14-22 | OiPr/H | Et | cyclohexyl-CO₂H (trans isomer, enantiomer 2) | +++ | 511 | HCl Salt |
| 14-23 | OiPr/H | cPr | cyclohexyl-CO₂H (trans isomer, enantiomer 1) | +++ | 523 | HCl Salt |

-continued

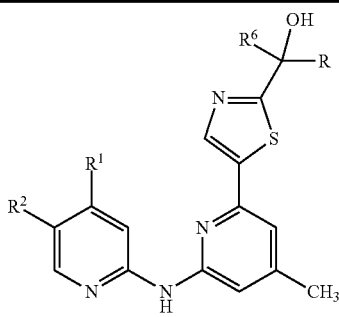

| Ex. | R¹/R² | R⁶ | R | rhSyk Activity | [M + H]+ Obs'd | Form(s) |
|---|---|---|---|---|---|---|
| 14-24 | OiPr/H | cPr | cyclohexyl-CO₂H (trans isomer, enantiomer 2) | +++ | 523 | HCl Salt |
| 14-25 | OiPr/H | CF₃ | cyclohexyl-CO₂H (trans isomer, enantiomer 1) | +++ | 551 | HCl Salt |
| 14-26 | OiPr/H | CF₃ | cyclohexyl-CO₂H (trans isomer, enantiomer 2) | +++ | 551 | HCl Salt |
| 14-27 | CF₃/H | H | cyclohexyl-CO₂Me (Racemic) | +++ | 507 | Free Base |
| 14-28 | CF₃/H | H | cyclohexyl-CO₂H (trans isomer, enantiomer 1) | +++ | 493 | Free Base |
| 14-29 | CF₃/H | H | cyclohexyl-CO₂H (trans isomer, enantiomer 2) | +++ | 493 | Free Base |
| 14-30 | CF₃/H | CH₃ | dimethylcyclohexyl-CO₂H (1S, 4R) Mixture of Isomers | +++ | 535 | TFA Salt |
| 14-31 | CF₃/H | CH₃ | dimethylcyclohexyl-CO₂H (1S, 4S), Isomer 1 | +++ | 535 | Free Base |

-continued
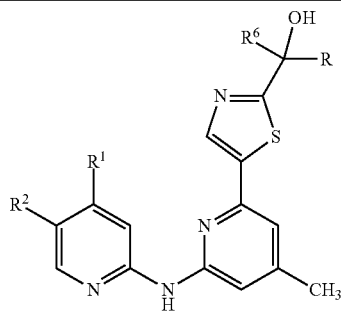
| Ex. | R¹/R² | R⁶ | R | rhSyk Activity | [M + H]+ Obs'd | Form(s) |
|---|---|---|---|---|---|---|
| 14-32 | CF₃/H | CH₃ | (1S, 4S), Isomer 2 | +++ | 535 | Free Base |
| 14-33 | CH₃/H | CH₃ | (1S, 4S), Isomer 1 | +++ | 481 | Free Base |
| 14-34 | CH₃/H | CH₃ | (1S, 4S), Isomer 2 | +++ | 481 | Free Base |
| 14-35 | OCH₃/H | CH₃ | (1S, 4S), Isomer 1 | +++ | 497 | TFA Salt |
| 14-36 | OCH₃/H | CH₃ | (1S, 4S), Isomer 2 | +++ | 497 | TFA Salt |
| 14-37 | CHF₂/H | CH₃ | (1S, 4S), Isomer 1 | +++ | 517 | TFA Salt |
| 14-38 | CHF₂/H | CH₃ | (1S, 4S), Isomer 2 | +++ | 517 | Free Base |

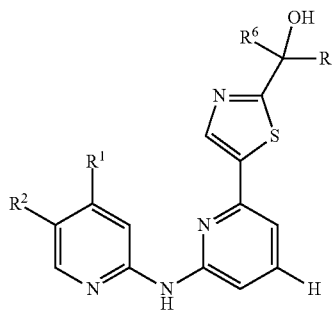

| Ex. | R¹/R² | R⁶ | R | rhSyk Activity | [M + H]+ Obs'd | Form(s) |
|---|---|---|---|---|---|---|
| 14-39 | CH₃/H | CH₃ | cyclohexane-CO₂H (trans isomer, enantiomer 1) | +++ | 439 | TFA Salt |
| 14-40 | CH₃/H | CH₃ | cyclohexane-CO₂H (trans isomer, enantiomer 2) | +++ | 439 | TFA Salt |
| 14-41 | OCH₃/H | CH₃ | cyclohexane-CO₂H (trans isomer, enantiomer 1) | +++ | 455 | Free base |
| 14-42 | CHF₂/H | CH₃ | cyclohexane-CO₂H (trans isomer, enantiomer 1) | +++ | 475 | Free Base |
| 14-43 | iPr/H | CH₃ | cyclohexane-CO₂H (trans isomer, enantiomer 1) | +++ | 467 | Free Base |
| 14-44 | CF₃/H | CH₃ | dimethylcyclohexane-CO₂H (1S, 4S), Isomer 1 | +++ | 521 | Free Base |
| 14-45 | CF₃/H | CH₃ | dimethylcyclohexane-CO₂H (1S, 4S), Isomer 2 | +++ | 521 | Free Base |
| 14-46 | CH₃/H | CH₃ | dimethylcyclohexane-CO₂H (1S, 4S), Isomer 1 | +++ | 467 | Free Base |

-continued
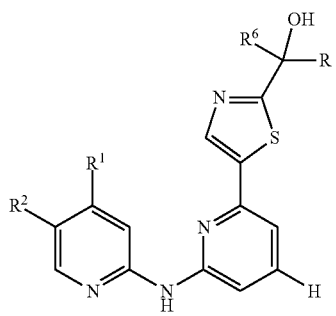
| Ex. | R¹/R² | R⁶ | R | rhSyk Activity | [M + H]+ Obs'd | Form(s) |
|---|---|---|---|---|---|---|
| 14-47 | CH₃/H | CH₃ | 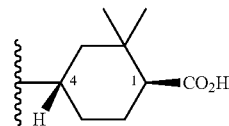 (1S, 4S), Isomer 2 | +++ | 467 | Free Base |
| 14-48 | OCH₃/H | CH₃ | 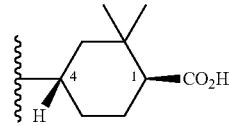 (1S, 4S), Isomer 1 | +++ | 483 | TFA Salt |
| 14-49 | OCH₃/H | CH₃ | 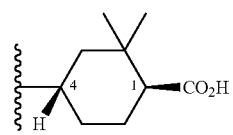 (1S, 4S), Isomer 2 | +++ | 483 | TFA Salt |
| 14-50 | CHF₂/H | CH₃ | 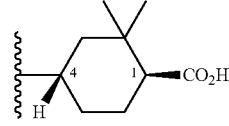 (1S, 4S), Isomer 1 | +++ | 503 | Free Base |
| 14-51 | CHF₂/H | CH₃ | 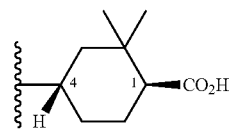 (1S, 4S), Isomer 2 | +++ | 503 | Free Base |

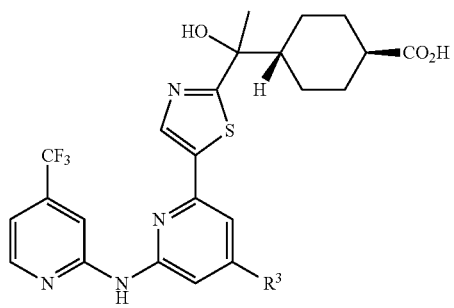

| Ex. | $R^3$ | Stereochemistry | rhSyk Activity | [M + H]+ Obs'd | Form(s) |
|---|---|---|---|---|---|
| 14-52 | Cl | (trans isomer, enantiomer 1) | +++ | 527 | TFA Salt |
| 14-53 | $CHF_2$ | (trans isomer, enantiomer 1) | +++ | 543 | TFA Salt |
| 14-54 | cPr | (trans isomer, enantiomer 1) | +++ | 533 | Free Base |

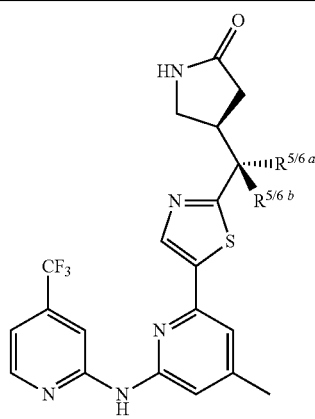

| Ex. | $R^{5/6a}$ | $R^{5/6b}$ | rhSyk Activity | [M + H]+ Obs'd | Form(s) |
|---|---|---|---|---|---|
| 14-55 | OH | $CH_3$ | +++ | 464 | Free Base |
| 14-46 | $CH_3$ | OH | +++ | 464 | Free Base |

Example 15

Stereoisomers of 4-{1-hydroxy-1-[5-(4-methyl-6-{[4-(trifluoromethyl)pyridin-2-yl]amino}pyridin-2-yl)-1,3-thiazol-2-yl]ethyl}-2-methylcyclohexanecarboxylic acid The following compounds were prepared in an analogous manner to that described in Example 14, steps 1 and 2 using the products from Intermediate 14, step 2. During step 2, isomerization sometimes occurred. When isomerization occurred, the isomers were separated and then tested. The table below indicates when isomerization was observed.

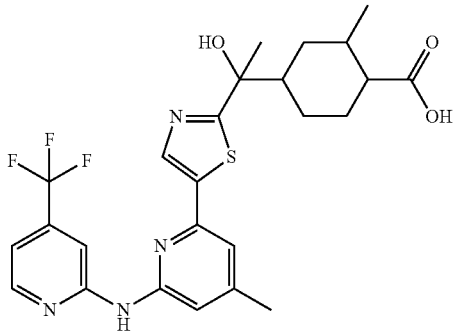 [SMILES: Cc1cc(Nc2cc(C(F)(F)F)ccn2)nc(-c2cnc(C(C)(O)C3CCC(C(=O)O)C(C)C3)s2)c1]

| Intermediate Used | Isomerization Observed? | Ex. | [M + H]+ Obs'd | rhSyk Activity | Form (s) |
|---|---|---|---|---|---|
| Intermediate 14, Step 2, Isomer 1 | Yes | 15-1 | 521 | +++ (Peak 1) | Free Base |
|  |  | 15-2 | 521 | +++ (Peak 2) | Free Base |
| Intermediate 14, Step 2, Isomer 2 | Yes | 15-3 | 521 | +++ (Peak 1) | Free Base |
|  |  | 15-4 | 521 | +++ (Peak 2) | Free Base |
| Intermediate 14, Step 2, Isomer 3 | Yes | 15-5 | 521 | +++ (Peak 1) | TFA Salt |
|  |  | 15-6 | 521 | +++ (Peak 2) | TFA Salt |
| Intermediate 14, Step 2, Isomer 4 | Yes | 15-7 | 521 | +++ (Peak 1) | Free Base |
|  |  | 15-8 | 521 | +++ (Peak 2) | Free Base |
| Intermediate 14, Step 2, Isomer 5 | No | 15-9 | 521 | +++ | Free Base |
| Intermediate 14, Step 2, Isomer 6 | No | 15-10 | 521 | +++ | Free Base |
| Intermediate 14, Step 2, Isomer 7 | No | 15-11 | 521 | +++ | Free Base |
| Intermediate 14, Step 2, Isomer 8 | No | 15-12 | 521 | +++ | TFA Salt |
| Intermediate 14, Step 2, Isomer 9 | No | 15-13 | 521 | +++ | TFA Salt |
| Intermediate 14, Step 2, Isomer 10 | No | 15-14 | 521 | +++ | Free Base |
| Intermediate 14, Step 2, Isomer 11 | No | 15-15 | 521 | +++ | Free Base |
| Intermediate 14, Step 2, Isomer 12 | No | 15-16 | 521 | +++ | Free Base |
| Intermediate 14, Step 2, Isomer 13 | No | 15-17 | 521 | +++ | Free Base |

What is claimed is:

1. A compound having the formula I:

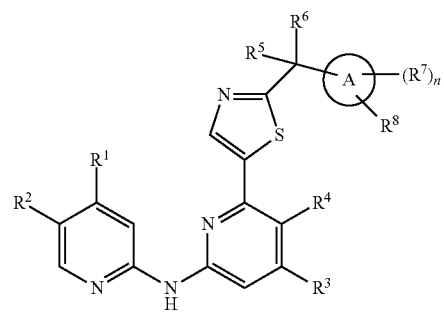

or a pharmaceutically acceptable salt thereof,
wherein

A is a carbocycle, or the moiety A-$(R^7)_n(R^8)$ represents

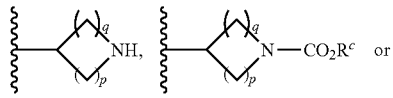

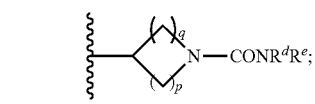

n is 0, 1, 2 or 3;

p and q are independently selected from 1, 2 and 3;

$R^1$ is $C_{1-4}$alkyl, $C_{1-4}$fluoroalkyl, $C_{3-6}$cycloalkyl or $C_{1-4}$alkoxy;

$R^2$ is H or halogen;

$R^3$ is H, halogen, $C_{1-4}$alkyl, $C_{1-4}$haloalkyl, $C_{3-6}$cycloalkyl or $C_{1-4}$hydroxyalkyl;

$R^4$ is H or halogen;

$R^5$ is OH, $C_{1-4}$alkoxy, halogen, $NH_2$; or $N(H)(C_{1-4}$alkyl);

$R^6$ is H, $C_{1-4}$alkyl, $C_{1-4}$haloalkyl, $C_{3-6}$cycloalkyl or $C_{1-4}$hydroxyalkyl;

$R^7$ is selected from OH and $C_{1-4}$alkyl;

$R^8$ is selected from $(CR^aR^b)_nCO_2R^c$, $CONR^dR^e$, tetrazolyl, OH, $CH_2OH$, oxo, CN, $NHCO_2R^f$ and $NHSO_2R^f$; with the proviso that $R^8$ and —$C(R^5)(R^6)$— are not attached to the same ring carbon atom;

$R^a$ and $R^b$ are each independently selected from H and methyl;

$R^c$ is H or $C_{1-4}$alkyl, $R^d$ and $R^e$ are each independently selected from H and $C_{1-4}$alkyl; and $R^f$ is $C_{1-4}$alkyl or benzyl.

2. The compound of claim 1 or a pharmaceutically acceptable salt thereof, wherein ring A is a carbocycle.

3. The compound of claim 1 or a pharmaceutically acceptable salt thereof, wherein A is $C_{3-6}$cycloalkyl.

4. The compound of claim 1 or a pharmaceutically acceptable salt thereof, wherein A is cyclohexyl.

5. The compound of claim 1 or a pharmaceutically acceptable salt thereof, wherein $R^5$ is OH.

6. The compound of claim 1 or a pharmaceutically acceptable salt thereof, wherein A is a carbocycle, and $R^8$ is selected from $(CR^aR^b)_nCO_2R^c$ and $C(O)NR^dR^e$.

7. The compound of claim 1 or a pharmaceutically acceptable salt thereof, wherein A is $C_{3-6}$cycloalkyl and $R^8$ is $CO_2R^c$.

8. The compound of claim 1 having the formula Ia:

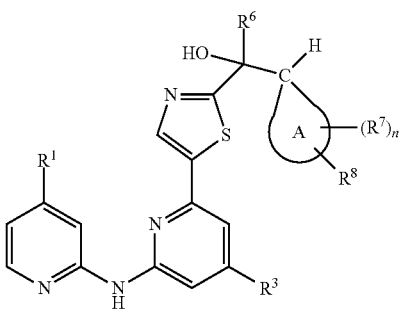

or a pharmaceutically acceptable salt thereof,
wherein

A is a carbocycle;

n is 0, 1 or 2;

$R^1$ is $C_{1-4}$alkyl or $C_{1-4}$fluoroalkyl;

$R^3$ is H, $C_{1-4}$alkyl, $C_{1-4}$haloalkyl or $C_{3-6}$cycloalkyl;

$R^6$ is H, $C_{1-4}$alkyl, $C_{1-4}$haloalkyl or $C_{3-4}$cycloalkyl;

$R^7$ is $C_{1-4}$alkyl;

$R^8$ is $CO_2R^c$ or $CONR^dR^e$;

$R^c$ is H or $C_{1-4}$alkyl, $R^d$ and $R^e$ are each independently selected from H and $C_{1-4}$alkyl.

9. The compound of claim 8 or a pharmaceutically acceptable salt thereof, wherein $R^3$ is $C_{1-4}$alkyl, $C_{1-4}$haloalkyl or $C_{3-6}$cycloalkyl; and $R^6$ is H, $C_{1-4}$alkyl, or $C_{1-4}$haloalkyl.

10. The compound of claim 1 having the formula Ib:

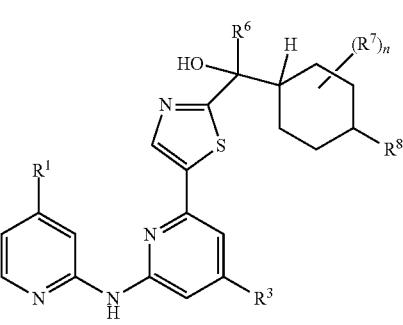

or a pharmaceutically acceptable salt thereof,
wherein n is 0, 1 or 2;

$R^1$ is $C_{1-4}$alkyl or $C_{1-4}$fluoroalkyl;

$R^3$ is H, $C_{1-4}$alkyl, $C_{1-4}$haloalkyl or $C_{3-6}$cycloalkyl;

$R^6$ is H, $C_{1-4}$alkyl, $C_{1-4}$haloalkyl or $C_{3-4}$cycloalkyl;

$R^7$ is $C_{1-4}$alkyl;

$R^8$ is $CO_2R^c$ or $CONR^dR^e$;

$R^c$ is H or $C_{1-4}$alkyl, $R^d$ and $R^e$ are each independently selected from H and $C_{1-4}$alkyl.

11. The compound of claim 10 or a pharmaceutically acceptable salt thereof, wherein $R^8$ is $CO_2R^c$.

12. The compound of claim 10 or a pharmaceutically acceptable salt thereof, wherein $R^3$ is $C_{1-4}$alkyl, $C_{1-4}$haloalkyl or $C_{3-6}$cycloalkyl; and $R^6$ is H, $C_{1-4}$alkyl or $C_{1-4}$haloalkyl.

13. A pharmaceutical composition comprising a therapeutically effective amount of a compound of claim 1 or a pharmaceutically acceptable salt thereof, and a pharmaceutically acceptable carrier.

* * * * *